United States Patent
Lee et al.

(10) Patent No.: US 9,963,722 B2
(45) Date of Patent: May 8, 2018

(54) STRAIN SECRETING FATTY ACIDS BY PHOSPHOLIPASE AND METHOD FOR PRODUCING FATTY ACIDS USING IT

(71) Applicant: SOGANG UNIVERSITY RESEARCH FOUNDATION, Seoul (KR)

(72) Inventors: Jeong Kug Lee, Seoul (KR); Eui Jin Kim, Seoul (KR); Xiaomeng Tong, Seoul (KR); Eun Kyung Oh, Gyeonggi-do (KR)

(73) Assignee: SOGANG UNIVERSITY RESEARCH FOUNDATION, Seoul (KR)

( * ) Notice: Subject to any disclaimer, the term of this patent is extended or adjusted under 35 U.S.C. 154(b) by 16 days.

(21) Appl. No.: 14/730,174

(22) Filed: Jun. 3, 2015

(65) Prior Publication Data
US 2016/0046968 A1   Feb. 18, 2016

(30) Foreign Application Priority Data
Jun. 3, 2014   (KR) .................. 10-2014-0067747

(51) Int. Cl.
*C12N 1/20* (2006.01)
*C12P 7/64* (2006.01)
(Continued)

(52) U.S. Cl.
CPC .............. *C12P 7/6409* (2013.01); *C12N 1/20* (2013.01); *C12N 9/1029* (2013.01); *C12N 9/18* (2013.01);
(Continued)

(58) Field of Classification Search
None
See application file for complete search history.

(56) References Cited

U.S. PATENT DOCUMENTS

| | | | |
|---|---|---|---|
| 2011/0165637 A1* | 7/2011 | Pfleger | C12N 9/16 435/134 |
| 2011/0250659 A1* | 10/2011 | Roberts | C12N 9/20 435/134 |

OTHER PUBLICATIONS

Deng et al., "A novel expression vector for high-level synthesis and secretion of foreign proteins in *Esherichia coli*: overproduciton of bovine pancreatic phospholipae A2", Gene, vol. 93, pp. 229-234, 1990.*

(Continued)

*Primary Examiner* — Richard C Ekstrom
(74) *Attorney, Agent, or Firm* — The PL Law Group, PLLC

(57) ABSTRACT

A bacterial strain secreting fatty acids, the strain inducing fatty acids to be extracellularly secreted by using phospholipase expressed in the periplasmic space of cell. When a method of producing fatty acids by using the bacterial strain secreting fatty acids is used, fatty acids extracellularly secreted are continuously obtained without apoptosis, leading to lower costs and higher production efficiency. Phospholipase, unlike thioesterase, which is a typical fatty-acid degrading enzyme, decomposes phospholipid to produce free fatty acids. Accordingly, by using the substrate specificity of two different phospholipases, a fatty acid having a specific composition can be selectively produced. Unlike in a typical method in which fat is obtained from cells or tissues, fatty acids secreted during cell growth are obtainable by biding to a hydrophobic material without an extraction process using an organic solvent in large quantities. Accordingly, a more economical, environmentally friendly bio-oil production process can be realized.

4 Claims, 8 Drawing Sheets

(51) Int. Cl.
  *C12N 9/20*   (2006.01)
  *C12N 9/10*   (2006.01)
  *C12N 9/00*   (2006.01)
  *C12N 9/18*   (2006.01)

(52) U.S. Cl.
  CPC ............... *C12N 9/20* (2013.01); *C12N 9/93* (2013.01); *C12Y 203/0118* (2013.01); *C12Y 203/01039* (2013.01); *C12Y 301/01004* (2013.01); *C12Y 301/01032* (2013.01); *C12Y 602/01003* (2013.01); *C12Y 604/01002* (2013.01); *C07K 2319/02* (2013.01)

(56) References Cited

OTHER PUBLICATIONS

UniProtKB-SwissProt Accession No. Q941 F1.2, published Jun. 26, 2013.*

Donohue et al., "Cloning, DNA sequence, and expression of the Rhodobacter sphaeroides cytochrome c2 gene", Journal of Bacteriology, vol. 168, No. 2, pp. 962-972, 1986.*

* cited by examiner

SEQUENCE LISTING

<160> NUMBER OF SEQ ID NOS: 39

<210> SEQ ID NO 1
<211> LENGTH: 1548
<212> TYPE: DNA
<213> ORGANISM: Arabidopsis thaliana

<400> SEQUENCE: 1

| atggcgacca ttccctccca caaccttcgt cctcatacga ccaaccaaag gactcagtac | 60 |
|---|---|
| tctctttcct tcagaccaca cttttcacgc tctactctga tcactttccc ggcaagatca | 120 |
| tcgccggcga gggctatgtc cagaaccgac gaggaggctt caatatctac aaggctcgag | 180 |
| caagaaagct atgggctgac gacggcagag gacattcgcc gacgggatgg agaagcaaaa | 240 |
| gaatccaaga ggttgagaga cacgtggcgg aagatccaag gggaagatga ttgggccggg | 300 |
| ttaatggatc cgatggaccc ggttctgaga tctgagctga tccggtacgg agaaatggcc | 360 |
| caggcctgtt acgacgcctt cgatttcgat ccattttcaa ggtactgcgg gagctgcaga | 420 |
| ttcacgcgcc gtcacttgtt cgattcgctc gggataatcg attctggcta tgaggtggcg | 480 |
| cgttatctct acgcgacgtc gaacatcaac cttcctaatt tcttctccaa atcgagatgg | 540 |
| tccaaggtgt ggagcaagaa cgccaattgg atgggttacg tggctgtatc cgacgacaac | 600 |
| gaagccacgc gctgccgttt aggacgccgc gacattgcca tcgcctggag agggactgtc | 660 |
| acgcggctcg agtggatagc tgatctcaag gatttcctca accggtatc cggaaacgga | 720 |
| ttccgatgcc ccgacccggc cgtaaaagcc gaatccgggt ttctggatct atacacggac | 780 |
| aaagatacat cctgcaattt ctccaaattc tcggcgcgag agcaggttct tacggaagtg | 840 |
| aagcggctgg tggaaaggta cggcgacgag gaaggagaag aactgagcat caccgtgacg | 900 |
| ggacacagtc tcggcggtgc gctggcggtg ctaagcgcgt acgacgtggc ggagatgggt | 960 |
| gtgaacagaa cgaggaaagg aaaagtgatt ccggtgacgg cgttcacgta cggaggaccg | 1020 |
| cgagttggga acattcgatt caaggagagg attgagaaat tgggagtgaa ggtgttgaga | 1080 |
| gtggtgaacg agcacgacgt cgtggcgaaa tcgccgggac tgtttctgaa cgagcgtgcg | 1140 |
| ccacaggcgc taatgaaatt ggcgggagga ttgccgtggt gctatagcca cgtgggagaa | 1200 |
| atgctgccgt tggatcatca gaagtctccg ttccttaagc ccaccgttga tcttttctacg | 1260 |
| gctcataact tggaagctct cctccatctc cttgacgggt atcatgggaa aggacagaga | 1320 |
| tttgtgttat caagtgggag agatccagcg ttagtgaaca aagcatctga tttttttgaaa | 1380 |
| gaccatttca tggtccctcc ttattggcgc caagacgcaa acaaagggat ggtgaggaac | 1440 |
| actgacggcc gttggattca acctgatcgc atccgtgcag atgatcaaca tgctcctgac | 1500 |
| atacatcaac tcctcaccca actccatcat ccatcacaac tcttgtaa | 1548 |

<210> SEQ ID NO 2
<211> LENGTH: 447
<212> TYPE: DNA
<213> ORGANISM: Arabidopsis thaliana

<400> SEQUENCE: 2

| atggcggctc cgatcatact tttctctttc cttttattct tctctgtctc tgtctcggca | 60 |
|---|---|
| cttaacgtcg gtgttcagct catacatccc tccatttcct tgactaaaga atgtagccgg | 120 |
| aaatgtgaat cagagttttg ttcagtgcct ccatttctga ggtatgggaa gtactgtgga | 180 |
| ctactttaca gtggatgtcc tggtgagaga ccttgtgatg tcttgattc tgttgcatg | 240 |
| aaacatgatg cttgtgtcca atccaagaat aatgattatc taagccaaga gtgtagtcag | 300 |

```
aagttcatta actgcatgaa caatttcagc cagaagaagc aaccgacgtt caaaggtaac    360
aaatgcgacg ctgatgaagt gattgatgtc atctccattg tcatggaagc tgctcttatc    420
gccggcaaag tcctcaagaa accctaa                                        447
```

<210> SEQ ID NO 3
<211> LENGTH: 28
<212> TYPE: DNA
<213> ORGANISM: Artificial Sequence
<220> FEATURE:
<223> OTHER INFORMATION: phospholipase A1 forward primer

<400> SEQUENCE: 3

```
gctctagaat gtcttctaca tgttcttc                                        28
```

<210> SEQ ID NO 4
<211> LENGTH: 27
<212> TYPE: DNA
<213> ORGANISM: Artificial Sequence
<220> FEATURE:
<223> OTHER INFORMATION: phospholipase A1 reverse primer

<400> SEQUENCE: 4

```
caagcttcta tacattagga agatgac                                         27
```

<210> SEQ ID NO 5
<211> LENGTH: 30
<212> TYPE: DNA
<213> ORGANISM: Artificial Sequence
<220> FEATURE:
<223> OTHER INFORMATION: phospholipase A2 forward primer

<400> SEQUENCE: 5

```
ctctagactt aacgtcggtg ttcagctcat                                      30
```

<210> SEQ ID NO 6
<211> LENGTH: 32
<212> TYPE: DNA
<213> ORGANISM: Artificial Sequence
<220> FEATURE:
<223> OTHER INFORMATION: phospholipase A2 reverse primer

<400> SEQUENCE: 6

```
caagctttta gggtttcttg aggactttgc cg                                   32
```

<210> SEQ ID NO 7
<211> LENGTH: 438
<212> TYPE: DNA
<213> ORGANISM: Rhodobacter sphaeroides

<400> SEQUENCE: 7

```
atgaagttcc aagtcaaggc cctcgccgcc atcgccgcat tcgcggcgct gccggcgctc    60
gcgcaggaag cgaccccgga agccggggcc aaggccttca accagtgcca gacctgccac    120
gtcatcgtgg acgattccgg caccaccatc gccggccgca acgccaagac cggcccgaac    180
ctctacggcg tcgtgggccg caccgcgggc acgcaggccg acttcaaggg ctatggcgaa    240
ggcatgaagg aagccggcgc gaaagggctc gcctgggatg aagagcattt cgtccagtat    300
gttcaggatc cgaccaagtt cctgaaggaa tataccggcg acgcgaaagc caagggcaag    360
atgaccttca agctgaagaa ggaagcggac gcccacaaca tctgggccta cctccagcag    420
gtcgccgtcc ggccctga                                                  438
```

<210> SEQ ID NO 8
<211> LENGTH: 145
<212> TYPE: PRT
<213> ORGANISM: Rhodobacter sphaeroides

<400> SEQUENCE: 8

```
Met Lys Phe Gln Val Lys Ala Leu Ala Ala Ile Ala Ala Phe Ala Ala
1               5                   10                  15

Leu Pro Ala Leu Ala Gln Glu Gly Asp Pro Glu Ala Gly Ala Lys Ala
            20                  25                  30

Phe Asn Gln Cys Gln Thr Cys His Val Ile Val Asp Asp Ser Gly Thr
        35                  40                  45

Thr Ile Ala Gly Arg Asn Ala Lys Thr Gly Pro Asn Leu Tyr Gly Val
    50                  55                  60

Val Gly Arg Thr Ala Gly Thr Gln Ala Asp Phe Lys Gly Tyr Gly Glu
65                  70                  75                  80

Gly Met Lys Glu Ala Gly Ala Lys Gly Leu Ala Trp Asp Glu Glu His
                85                  90                  95

Phe Val Gln Tyr Val Gln Asp Pro Thr Lys Phe Leu Lys Glu Tyr Thr
            100                 105                 110

Gly Asp Ala Lys Ala Lys Gly Lys Met Thr Phe Lys Leu Lys Lys Glu
        115                 120                 125

Ala Asp Ala His Asn Ile Trp Ala Tyr Leu Gln Gln Val Ala Val Arg
    130                 135                 140

Pro
145
```

<210> SEQ ID NO 9
<211> LENGTH: 22
<212> TYPE: DNA
<213> ORGANISM: Artificial Sequence
<220> FEATURE:
<223> OTHER INFORMATION: CycA leader forward primer

<400> SEQUENCE: 9
cccatggatg aagttccaag tc                                          22

<210> SEQ ID NO 10
<211> LENGTH: 32
<212> TYPE: DNA
<213> ORGANISM: Artificial Sequence
<220> FEATURE:
<223> OTHER INFORMATION: CycA leader reverse primer

<400> SEQUENCE: 10
ctctagacgc gagcgccggc agcgccgcga at                               32

<210> SEQ ID NO 11
<211> LENGTH: 515
<212> TYPE: PRT
<213> ORGANISM: Arabidopsis thaliana

<400> SEQUENCE: 11

```
Met Ala Thr Ile Pro Ser His Asn Leu Arg Pro His Thr Thr Asn Gln
1               5                   10                  15

Arg Thr Gln Tyr Ser Leu Ser Phe Arg Pro His Phe Ser Arg Ser Thr
            20                  25                  30

Leu Ile Thr Phe Pro Ala Arg Ser Ser Pro Ala Arg Ala Met Ser Arg
        35                  40                  45
```

-continued

```
Thr Asp Glu Glu Ala Ser Ile Ser Thr Arg Leu Glu Gln Glu Ser Tyr
    50                  55                  60

Gly Leu Thr Thr Ala Glu Asp Ile Arg Arg Asp Gly Glu Ala Lys
65                  70                  75                  80

Glu Ser Lys Arg Leu Arg Asp Thr Trp Arg Lys Ile Gln Gly Glu Asp
                85                  90                  95

Asp Trp Ala Gly Leu Met Asp Pro Met Asp Pro Val Leu Arg Ser Glu
                100                 105                 110

Leu Ile Arg Tyr Gly Glu Met Ala Gln Ala Cys Tyr Asp Ala Phe Asp
                115                 120                 125

Phe Asp Pro Phe Ser Arg Tyr Cys Gly Ser Cys Arg Phe Thr Arg Arg
130                 135                 140

His Leu Phe Asp Ser Leu Gly Ile Ile Asp Ser Gly Tyr Glu Val Ala
145                 150                 155                 160

Arg Tyr Leu Tyr Ala Thr Ser Asn Ile Asn Leu Pro Asn Phe Phe Ser
                165                 170                 175

Lys Ser Arg Trp Ser Lys Val Trp Ser Lys Asn Ala Asn Trp Met Gly
                180                 185                 190

Tyr Val Ala Val Ser Asp Asp Asn Glu Ala Thr Arg Cys Arg Leu Gly
                195                 200                 205

Arg Arg Asp Ile Ala Ile Ala Trp Arg Gly Thr Val Thr Arg Leu Glu
210                 215                 220

Trp Ile Ala Asp Leu Lys Asp Phe Leu Lys Pro Val Ser Gly Asn Gly
225                 230                 235                 240

Phe Arg Cys Pro Asp Pro Ala Val Lys Ala Glu Ser Gly Phe Leu Asp
                245                 250                 255

Leu Tyr Thr Asp Lys Asp Thr Ser Cys Asn Phe Ser Lys Phe Ser Ala
                260                 265                 270

Arg Glu Gln Val Leu Thr Glu Val Lys Arg Leu Val Glu Arg Tyr Gly
                275                 280                 285

Asp Glu Glu Gly Glu Leu Ser Ile Thr Val Thr Gly His Ser Leu
                290                 295                 300

Gly Gly Ala Leu Ala Val Leu Ser Ala Tyr Asp Val Ala Glu Met Gly
305                 310                 315                 320

Val Asn Arg Thr Arg Lys Gly Lys Val Ile Pro Val Thr Ala Phe Thr
                325                 330                 335

Tyr Gly Gly Pro Arg Val Gly Asn Ile Arg Phe Lys Glu Arg Ile Glu
                340                 345                 350

Lys Leu Gly Val Lys Val Leu Arg Val Val Asn Glu His Asp Val Val
                355                 360                 365

Ala Lys Ser Pro Gly Leu Phe Leu Asn Glu Arg Ala Pro Gln Ala Leu
                370                 375                 380

Met Lys Leu Ala Gly Gly Leu Pro Trp Cys Tyr Ser His Val Gly Glu
385                 390                 395                 400

Met Leu Pro Leu Asp His Gln Lys Ser Pro Phe Leu Lys Pro Thr Val
                405                 410                 415

Asp Leu Ser Thr Ala His Asn Leu Glu Ala Leu Leu His Leu Leu Asp
                420                 425                 430

Gly Tyr His Gly Lys Gly Gln Arg Phe Val Leu Ser Ser Gly Arg Asp
                435                 440                 445

Pro Ala Leu Val Asn Lys Ala Ser Asp Phe Leu Lys Asp His Phe Met
450                 455                 460

Val Pro Pro Tyr Trp Arg Gln Asp Ala Asn Lys Gly Met Val Arg Asn
```

```
                465                 470                 475                 480
Thr Asp Gly Arg Trp Ile Gln Pro Asp Arg Ile Arg Ala Asp Gln
                        485                 490                 495
His Ala Pro Asp Ile His Gln Leu Leu Thr Gln Leu His His Pro Ser
                500                 505                 510
Gln Leu Leu
        515

<210> SEQ ID NO 12
<211> LENGTH: 148
<212> TYPE: PRT
<213> ORGANISM: Arabidopsis thaliana

<400> SEQUENCE: 12

Met Ala Ala Pro Ile Ile Leu Phe Ser Phe Leu Leu Phe Phe Ser Val
1               5                   10                  15
Ser Val Ser Ala Leu Asn Val Gly Val Gln Leu Ile His Pro Ser Ile
            20                  25                  30
Ser Leu Thr Lys Glu Cys Ser Arg Lys Cys Glu Ser Glu Phe Cys Ser
        35                  40                  45
Val Pro Pro Phe Leu Arg Tyr Gly Lys Tyr Cys Gly Leu Leu Tyr Ser
    50                  55                  60
Gly Cys Pro Gly Glu Arg Pro Cys Asp Gly Leu Asp Ser Cys Cys Met
65                  70                  75                  80
Lys His Asp Ala Cys Val Gln Ser Lys Asn Asn Asp Tyr Leu Ser Gln
                85                  90                  95
Glu Cys Ser Gln Lys Phe Ile Asn Cys Met Asn Asn Phe Ser Gln Lys
            100                 105                 110
Lys Gln Pro Thr Phe Lys Gly Asn Lys Cys Asp Ala Asp Glu Val Ile
        115                 120                 125
Asp Val Ile Ser Ile Val Met Glu Ala Ala Leu Ile Ala Gly Lys Val
    130                 135                 140
Leu Lys Lys Pro
145

<210> SEQ ID NO 13
<211> LENGTH: 960
<212> TYPE: DNA
<213> ORGANISM: Rhodobacter sphaeroides

<400> SEQUENCE: 13
atgaactatc tcgaattcga aaagccgctg tccgagatcg agggcaaggc cgaggagttg      60
cgcgcgctcg cgcggggcaa cagggagatg gacgtcgaga aggaagcgtc ggcgctcgac     120
aagaaggccg agacgctgct gaaggatctc tacaaggacc tgaccccctg gcggaagtgc     180
caggtggcgc gccatcccga ccgcccgcac tgcaaggact atatcgaggg cctcttcacc     240
gaatatacgc cgctcgcggg cgaccggaac ttcgccgacg accatgcgat catgggcggg     300
ctcgcgcggt tcaacgacaa tccggtggtg gtgatcggtc aggagaaggg ccacgacacc     360
aagacccgga tcgagcgcaa cttcggcatg gcccgccccg agggctatcg caaagccatc     420
cggctgatgg agatggcgca ccgcttccgg ctgccggtca tcacgctcgt ggatacgccc     480
ggcgcctatc ccggcaaggg tgcggaagag cgcggccagg ccgaggccat gcgcgggcc      540 acgcagaaat gcctcgagat cggcgtgccg ctggtggcgg tggtgatcgg cgagggcggc     600
tcgggcgggg cggtggcgct ggccacggcg aaccggatcg ccatgctcga acattcggtc     660
```

| | |
|---|---|
| tattcggtga tctcgcccga gggctgcgcc tcgatcctgt ggaaggatgc cgagaagatg | 720 |
| cgcgaagccg ccgaagccct gcggctgacc gcgcaggatc tccacaagct cggcgtgatc | 780 |
| gaccggatca tcaaggagcc gctcggcggg gcgcagcgcg acgccgcga acggtcgac | 840 |
| gccgtgggca aggccatcga gatgatgctg aaggagctgg tggccgcaa gcccgagtgg | 900 |
| ctcgtgaagg atcggcgcaa caagttcctc gacatggggt cgaagggcct cgcggcgtga | 960 |

```
<210> SEQ ID NO 14
<211> LENGTH: 495
<212> TYPE: DNA
<213> ORGANISM: Rhodobacter sphaeroides

<400> SEQUENCE: 14
```

| | |
|---|---|
| atgagcaaga acaacaccga ggccgatgtc gccttcatcc aggcccttgc cgaactgctg | 60 |
| aacagcaacg agctcacgga actttcggtc aaacgggaat atggcgagga cgacagcctc | 120 |
| gaggtccgcg tggtcaagca ggccaacatc gtgacgaccc aggttgcggc gccgatgatg | 180 |
| gccgccgccc ccgcggcgat gccggcggtc ggcggtgccc ccgccgccgc tccggccgcg | 240 |
| gtcgaggatc cggcccagca tccgggcgcc gtcacctcgc ccatggtggg caccgtctat | 300 |
| atcgcccccg agcgggcgc ctcgcccttc gtcaccgtgg cgccaccgt gaccgagggg | 360 |
| cagacgctcc tcatcatcga ggcgatgaag accatgaacc acatcccgc ccgcgcgcg | 420 |
| ggcacggtga gcgggtcct cgtctcggac ggcacggcgg tcgaatacgg cgcgcccctc | 480 |
| atgatcatcg agtga | 495 |

```
<210> SEQ ID NO 15
<211> LENGTH: 1347
<212> TYPE: DNA
<213> ORGANISM: Rhodobacter sphaeroides

<400> SEQUENCE: 15
```

| | |
|---|---|
| atgttcgaaa agatcctgat cgccaaccgc ggcgagatcg ccttgcgcgt gatccgcgcc | 60 |
| tgccaggaga tggggatcaa gtcggtcgcc gtccattcga ccgcggacgc cgatgccatg | 120 |
| catgtccgca tggccgatga gagcgtctgc atcggccgg cctcctcgac cgacagctat | 180 |
| ctcaacaagg cctcgatcat ctcggcctgc gagatcaccg gggccgaggc cgtccatccg | 240 |
| ggttacgggct tcctctccga gaacgcggcc ttcgcccagg cgctgcagga ccacgggatc | 300 |
| gagttcatcg gcccgaccgc ggaccatatc cgcatcatgg gcgacaagat caccgccaag | 360 |
| gacacgatga aggctctggg cgtgccctgc gtgcccggct ccgacggcgg cgtgcccgac | 420 |
| tacgagacgg ccatcgccac ggccagagac atcggcttcc cggtcatcat caaggccacg | 480 |
| gcgggcggcg gcgggcgcgg catgaaggtc gcgcggaacg agcaggaact cgagatcgcc | 540 |
| ttccgcaccg cgcgttcgga agccaaggcc gccttcggca acgacgaagt ctatatggag | 600 |
| aaatatctcc agaagccgcg gcacatcgag atccaggtgt cggcgacgg caagggccgc | 660 |
| gcggtccatc tgggcgagcg tgactgctcg ctgcagcggc ggcaccagaa ggtgttcgag | 720 |
| gaagccccgg gtccggtcat caccccccgag atgcgtgcgg agatcggcag gatctgcgcc | 780 |
| gacgcggtgg cgcggatcaa ctacatcggc gcgggcacga tcgaattcct ctacgaggac | 840 |
| ggccagttct acttcatcga gatgaacacc cgcctgcagg tggagcatcc ggtgaccgag | 900 |
| gcgatcttcg gcgtcgatct cgtcgcgag cagatccggg tcgcggcggg cctgccgatg | 960 |
| agcttcaatc aggatgcgct ggagatcaac ggccacgcca tcgaggtgcg gatcaacgcc | 1020 |
| gagaagctgc cgaacttttc gccctgcccc ggcaaggtgc gggtcttcca cgcgccgggc | 1080 |

```
ggcctcgggg tgcggatgga ttcggccctc tatggcggct attccatccc gccctattac    1140
gacagcctga tcggcaagct gatcgtgcac ggccgcgacc ggcccgaggc gctggcgcgc    1200
ctgcaccgcg ccctgggcga gctgatcgtg acgggatcg acacgacggt gccgctgttc     1260
cacgcgcttc tggccgagcc cgacatccag aatggcgact acaatatcca ctggctggaa    1320
aaatggctcg ccgcccagtt cggctga                                        1347
```

<210> SEQ ID NO 16
<211> LENGTH: 954
<212> TYPE: DNA
<213> ORGANISM: Rhodobacter sphaeroides

<400> SEQUENCE: 16

```
atgaactgga tctccaacta cgtccgcccg aagatcaact cgctctttc gcgccgcgag      60 gtgccggaga acctctggac caagtgcccg gagtgcggga cgatgctctt ccaccgcgag    120
ctggccgaga acctgaacgt ctgctccacc tgcgaccacc acatgaacat cagcccgcgg    180
gaccggttcg ccgcgctctt cgacggcggg atcttcaccg aggtcgaggt gccggtgccg    240
ctcgccgacc cgctccagtt ccgcgaccag aagcgctatc cgaccggat gaaggcggcg     300 cagaagacca cgggcgagaa ggaagccatg ctggtcgtcg agggcgagat cgcccggacg    360
caggtggtgg ccgcggccca ggacttcagc ttcatggcgg gctccatggg catgtatgtg    420
ggcaatgcca tcatcgccgc cgccgagcgc gcggtgaagc tcaaatgccc gctcatcctg    480
tttgccgccg ccggcggcgc gcggatgcag gagggatct tgtcgctcat gcagatgccg      540
cgcacgacgg tggcggtgca gatgctgcgc gaggcgggcc tgccctacat ctgcatcctg    600 acccaccccga ccacgggcgg cgtcaccgcc tcctatgcga tgctgggcga cgtgcagatc    660
gccgagccca atgcgctgat ctgcttcgcc ggccccgcg tgatcgagca gacgatccgc     720
gagaagctgc ccgagggctt ccagcgcgcc gaatatctgc tcgaccacgg gatgctcgac    780
cgggtgaccc accgcaaggc gatgcgcgag gagctggtca ccatcatccg gatgctgatg    840
aaccagccgc cggcgatcaa gggcgacctg cctgcgcccg agccgaagcc ggtgatcgac    900
ctgccgccgc cgccgacgcc ggaggcggtg gtcgacgaca aggccgccga gtga           954
```

<210> SEQ ID NO 17
<211> LENGTH: 933
<212> TYPE: DNA
<213> ORGANISM: Rhodobacter sphaeroides

<400> SEQUENCE: 17

```
atgagccgcg cattcgtgtt ccccgggcag ggcgctcaga ccatcggcat gggccgcgcg      60
ctcgccgaag cctatcctgc ggcgcgggcg gtattcgacg aggtggacga ggcgctcggc    120
gagaaactct cggcgctgat ctgggacgga tccatcgagg agctcacgct gacgcagaac    180
gcgcagcccg cgctgatggc gacctcgatg cggccctcg cggcgctcga ggtcgaaggc    240
ctgggcatcg ccaccgcctc cttcgtggcg ggtcactcgc tcggcgaata ttccgccctg    300
tgcgcggcga agtcgctgaa gctctcggat acgcgcgggc ttctgcgcat ccgcgggcag    360
gccatgcagg aggcggtgcc ggtgggcgtg gcgcgatgg ccgcgctcct cgggctcgat     420
tacgacaccg cggtcgaggt cgcgcacgag gcggcgcagg gcgaagtgtg ccaggccgcc    480
aacgacaacg atccggcgca ggtggtggtc tcgggccaca aggcggccgt cgagagggca    540
gtggagatcg ccaagggccg cggcgccaag cgggccatcc tgctgccggt gagcgccccc    600
```

-continued

```
ttccattgcg cactgatgca gcatgccgcg agcgtcatgt ccgaagctct cgccgcggtg    660
gtgatcgagg cgccggtctg cccggtcgtc gtgaacgtgc gcgccgaggc ggtgtcggag    720
ccggaccgga tccgtgcgct cctcgtggca caggtgacgg gggccgtccg ctggcgcgag    780
agcgtgatgt ggatggaaaa tgcgggcgtg acgagttct gggaaatcgg tgccggcaag    840
gcgctgtcgg gcatgatcaa gcggatcgcc aagggcgcgg cgacccgggc catcggcacg    900
cccgaggatg tggcggctgc cgccacggcc tga                               933
```

<210> SEQ ID NO 18
<211> LENGTH: 972
<212> TYPE: DNA
<213> ORGANISM: Rhodobacter sphaeroides

<400> SEQUENCE: 18

```
atgacaatac gcgccgtggt gagggcgtc gggcactatc tgcccgaccg tgtcgtcccg     60
aactccgaac tcgaggcgat cgtcgagacg accgacgaat ggatccgcac ccggtcgggc    120
atcgaacggc ggcatttcgc ggcggaggga cagacgacct ccgacctcgc cgcccgcgcg    180
gcgcgtgcag cgctcgagga cgcggggctt cagccggacg acatcgacac gctgatcgtc    240
gccacctcca cggccgatct caccttcccc tccgccgcca ccatggtgca ggcggccttg    300
ggcatgaccc gcggcttcgc cttcgacgtg caggcggtct gcgcgggctt cgtctatgcg    360
ctggccaatg ccgatgcgct gatccgctcg ggtcaggcgc agcgcgtgct cgtgatcggg    420
gccgagacct tcagccgcct gatggactgg aacgaccggg ccacctgcgt gctcttcggc    480
gatggcgcgg gcgcggtggt gctcgagggc accgagagcg ccggcacctc cgccgaccgc    540
ggcatccttg cgaccgacct gcattcggac ggccgcttca aggacctgct ctatgtcgat    600
ggcggctcct cgaccggcac cacgggccac ctgcggatgc agggacgcga ggttttccgc    660
catgccgttg agaagcttgc agaaacagcg catacggcac tggagaaggc gggcctcggc    720
gccggcgatg tcgactggat cgtgccgcat caggccaacc tgcgcatcat ctcggccacc    780
gcccagcgga tgcaggttcc gatggaccgc gtgatcctga cggtgcagga tcacggcaat    840
acctcggccg cctcgattcc cctggccctc tcggtcggca aggcacgcgg gcagatcaag    900
gaaggcgacc ttctggtcac cgaagcgatc ggcggcgggc tcgcctgggg ctcggtggtc    960
ctccgctggt ag                                                       972
```

<210> SEQ ID NO 19
<211> LENGTH: 319
<212> TYPE: PRT
<213> ORGANISM: Rhodobacter sphaeroides

<400> SEQUENCE: 19

```
Met Asn Tyr Leu Glu Phe Glu Lys Pro Leu Ser Glu Ile Glu Gly Lys
1               5                   10                  15

Ala Glu Glu Leu Arg Ala Leu Ala Arg Gly Asn Arg Glu Met Asp Val
            20                  25                  30

Glu Lys Glu Ala Ser Ala Leu Asp Lys Lys Ala Glu Thr Leu Leu Lys
        35                  40                  45

Asp Leu Tyr Lys Asp Leu Thr Pro Trp Arg Lys Cys Gln Val Ala Arg
    50                  55                  60

His Pro Asp Arg Pro His Cys Lys Asp Tyr Ile Glu Gly Leu Phe Thr
65                  70                  75                  80

Glu Tyr Thr Pro Leu Ala Gly Asp Arg Asn Phe Ala Asp Asp His Ala
                85                  90                  95
```

```
Ile Met Gly Gly Leu Ala Arg Phe Asn Asp Asn Pro Val Val Ile
            100                 105                 110

Gly Gln Glu Lys Gly His Asp Thr Lys Thr Arg Ile Glu Arg Asn Phe
        115                 120                 125

Gly Met Ala Arg Pro Glu Gly Tyr Arg Lys Ala Ile Arg Leu Met Glu
    130                 135                 140

Met Ala His Arg Phe Arg Leu Pro Val Ile Thr Leu Val Asp Thr Pro
145                 150                 155                 160

Gly Ala Tyr Pro Gly Lys Gly Ala Glu Glu Arg Gly Gln Ala Glu Ala
                165                 170                 175

Ile Ala Arg Ala Thr Gln Lys Cys Leu Glu Ile Gly Val Pro Leu Val
            180                 185                 190

Ala Val Val Ile Gly Glu Gly Gly Ser Gly Gly Ala Val Ala Leu Ala
        195                 200                 205

Thr Ala Asn Arg Ile Ala Met Leu Glu His Ser Val Tyr Ser Val Ile
    210                 215                 220

Ser Pro Glu Gly Cys Ala Ser Ile Leu Trp Lys Asp Ala Glu Lys Met
225                 230                 235                 240

Arg Glu Ala Ala Glu Ala Leu Arg Leu Thr Ala Gln Asp Leu His Lys
                245                 250                 255

Leu Gly Val Ile Asp Arg Ile Ile Lys Glu Pro Leu Gly Gly Ala Gln
            260                 265                 270

Arg Gly Arg Arg Glu Thr Val Asp Ala Val Gly Lys Ala Ile Glu Met
        275                 280                 285

Met Leu Lys Glu Leu Val Gly Arg Lys Pro Glu Trp Leu Val Lys Asp
    290                 295                 300

Arg Arg Asn Lys Phe Leu Asp Met Gly Ser Lys Gly Leu Ala Ala
305                 310                 315

<210> SEQ ID NO 20
<211> LENGTH: 164
<212> TYPE: PRT
<213> ORGANISM: Rhodobacter sphaeroides

<400> SEQUENCE: 20

Met Ser Lys Asn Asn Thr Glu Ala Asp Val Ala Phe Ile Gln Ala Leu
1               5                   10                  15

Ala Glu Leu Leu Asn Ser Asn Glu Leu Thr Glu Leu Ser Val Lys Arg
            20                  25                  30

Glu Tyr Gly Glu Asp Asp Ser Leu Glu Val Arg Val Val Lys Gln Ala
        35                  40                  45

Asn Ile Val Thr Thr Gln Val Ala Ala Pro Met Met Ala Ala Ala Pro
    50                  55                  60

Ala Ala Met Pro Ala Val Gly Gly Ala Pro Ala Ala Ala Pro Ala Ala
65                  70                  75                  80

Val Glu Asp Pro Ala Gln His Pro Gly Ala Val Thr Ser Pro Met Val
                85                  90                  95

Gly Thr Val Tyr Ile Ala Pro Glu Pro Gly Ala Ser Pro Phe Val Thr
            100                 105                 110

Val Gly Ala Thr Val Thr Glu Gly Gln Thr Leu Leu Ile Ile Glu Ala
        115                 120                 125

Met Lys Thr Met Asn His Ile Pro Ala Pro Arg Ala Gly Thr Val Lys
    130                 135                 140

Arg Val Leu Val Ser Asp Gly Thr Ala Val Glu Tyr Gly Ala Pro Leu
```

Met Ile Ile Glu

<210> SEQ ID NO 21
<211> LENGTH: 448
<212> TYPE: PRT
<213> ORGANISM: Rhodobacter sphaeroides

<400> SEQUENCE: 21

Met Phe Glu Lys Ile Leu Ile Ala Asn Arg Gly Glu Ile Ala Leu Arg
1               5                   10                  15

Val Ile Arg Ala Cys Gln Glu Met Gly Ile Lys Ser Val Ala Val His
            20                  25                  30

Ser Thr Ala Asp Ala Asp Ala Met His Val Arg Met Ala Asp Glu Ser
        35                  40                  45

Val Cys Ile Gly Pro Ala Ser Ser Thr Asp Ser Tyr Leu Asn Lys Ala
    50                  55                  60

Ser Ile Ile Ser Ala Cys Glu Ile Thr Gly Ala Glu Ala Val His Pro
65                  70                  75                  80

Gly Tyr Gly Phe Leu Ser Glu Asn Ala Ala Phe Ala Gln Ala Leu Gln
                85                  90                  95

Asp His Gly Ile Glu Phe Ile Gly Pro Thr Ala Asp His Ile Arg Ile
            100                 105                 110

Met Gly Asp Lys Ile Thr Ala Lys Asp Thr Met Lys Ala Leu Gly Val
        115                 120                 125

Pro Cys Val Pro Gly Ser Asp Gly Gly Val Pro Asp Tyr Glu Thr Ala
    130                 135                 140

Ile Ala Thr Ala Arg Asp Ile Gly Phe Pro Val Ile Ile Lys Ala Thr
145                 150                 155                 160

Ala Gly Gly Gly Gly Arg Gly Met Lys Val Ala Arg Asn Glu Gln Glu
                165                 170                 175

Leu Glu Ile Ala Phe Arg Thr Ala Arg Ser Glu Ala Lys Ala Ala Phe
            180                 185                 190

Gly Asn Asp Glu Val Tyr Met Glu Lys Tyr Leu Gln Lys Pro Arg His
        195                 200                 205

Ile Glu Ile Gln Val Phe Gly Asp Gly Lys Gly Arg Ala Val His Leu
    210                 215                 220

Gly Glu Arg Asp Cys Ser Leu Gln Arg Arg His Gln Lys Val Phe Glu
225                 230                 235                 240

Glu Ala Pro Gly Pro Val Ile Thr Pro Glu Met Arg Ala Glu Ile Gly
                245                 250                 255

Arg Ile Cys Ala Asp Ala Val Ala Arg Ile Asn Tyr Ile Gly Ala Gly
            260                 265                 270

Thr Ile Glu Phe Leu Tyr Glu Asp Gly Gln Phe Tyr Phe Ile Glu Met
        275                 280                 285

Asn Thr Arg Leu Gln Val Glu His Pro Val Thr Glu Ala Ile Phe Gly
    290                 295                 300

Val Asp Leu Val Arg Glu Gln Ile Arg Val Ala Ala Gly Leu Pro Met
305                 310                 315                 320

Ser Phe Asn Gln Asp Ala Leu Glu Ile Asn Gly His Ala Ile Glu Val
                325                 330                 335

Arg Ile Asn Ala Glu Lys Leu Pro Asn Phe Ser Pro Cys Pro Gly Lys
            340                 345                 350

Val Arg Val Phe His Ala Pro Gly Gly Leu Gly Val Arg Met Asp Ser

```
                355                 360                 365
Ala Leu Tyr Gly Gly Tyr Ser Ile Pro Pro Tyr Tyr Asp Ser Leu Ile
    370                 375                 380

Gly Lys Leu Ile Val His Gly Arg Asp Arg Pro Glu Ala Leu Ala Arg
385                 390                 395                 400

Leu His Arg Ala Leu Gly Glu Leu Ile Val Asp Gly Ile Asp Thr Thr
                405                 410                 415

Val Pro Leu Phe His Ala Leu Leu Ala Glu Pro Asp Ile Gln Asn Gly
            420                 425                 430

Asp Tyr Asn Ile His Trp Leu Glu Lys Trp Leu Ala Ala Gln Phe Gly
        435                 440                 445

<210> SEQ ID NO 22
<211> LENGTH: 317
<212> TYPE: PRT
<213> ORGANISM: Rhodobacter sphaeroides

<400> SEQUENCE: 22

Met Asn Trp Ile Ser Asn Tyr Val Arg Pro Lys Ile Asn Ser Leu Phe
1               5                   10                  15

Ser Arg Arg Glu Val Pro Glu Asn Leu Trp Thr Lys Cys Pro Glu Cys
            20                  25                  30

Gly Thr Met Leu Phe His Arg Glu Leu Ala Glu Asn Leu Asn Val Cys
        35                  40                  45

Ser Thr Cys Asp His His Met Asn Ile Ser Pro Arg Asp Arg Phe Ala
    50                  55                  60

Ala Leu Phe Asp Gly Gly Ile Phe Thr Glu Val Pro Val Pro
65                  70                  75                  80

Leu Ala Asp Pro Leu Gln Phe Arg Asp Gln Lys Arg Tyr Pro Asp Arg
                85                  90                  95

Met Lys Ala Ala Gln Lys Thr Thr Gly Glu Lys Glu Ala Met Leu Val
            100                 105                 110

Val Glu Gly Glu Ile Ala Arg Thr Gln Val Val Ala Ala Gln Asp
        115                 120                 125

Phe Ser Phe Met Ala Gly Ser Met Gly Met Tyr Val Gly Asn Ala Ile
    130                 135                 140

Ile Ala Ala Ala Glu Arg Ala Val Lys Leu Lys Cys Pro Leu Ile Leu
145                 150                 155                 160

Phe Ala Ala Ala Gly Gly Ala Arg Met Gln Glu Gly Ile Leu Ser Leu
                165                 170                 175

Met Gln Met Pro Arg Thr Thr Val Ala Val Gln Met Leu Arg Glu Ala
            180                 185                 190

Gly Leu Pro Tyr Ile Cys Ile Leu Thr His Pro Thr Thr Gly Gly Val
        195                 200                 205

Thr Ala Ser Tyr Ala Met Leu Gly Asp Val Gln Ile Ala Glu Pro Asn
    210                 215                 220

Ala Leu Ile Cys Phe Ala Gly Pro Arg Val Ile Glu Gln Thr Ile Arg
225                 230                 235                 240

Glu Lys Leu Pro Glu Gly Phe Gln Arg Ala Glu Tyr Leu Leu Asp His
                245                 250                 255

Gly Met Leu Asp Arg Val Thr His Arg Lys Ala Met Arg Glu Glu Leu
            260                 265                 270

Val Thr Ile Ile Arg Met Leu Met Asn Gln Pro Pro Ala Ile Lys Gly
        275                 280                 285
```

Asp Leu Pro Ala Pro Glu Pro Lys Pro Val Ile Asp Leu Pro Pro Pro
    290                 295                 300

Pro Thr Pro Glu Ala Val Val Asp Asp Lys Ala Ala Glu
305                 310                 315

<210> SEQ ID NO 23
<211> LENGTH: 310
<212> TYPE: PRT
<213> ORGANISM: Rhodobacter sphaeroides

<400> SEQUENCE: 23

Met Ser Arg Ala Phe Val Phe Pro Gly Gln Gly Ala Gln Thr Ile Gly
1               5                   10                  15

Met Gly Arg Ala Leu Ala Glu Ala Tyr Pro Ala Ala Arg Ala Val Phe
                20                  25                  30

Asp Glu Val Asp Glu Ala Leu Gly Glu Lys Leu Ser Ala Leu Ile Trp
            35                  40                  45

Asp Gly Ser Ile Glu Glu Leu Thr Leu Thr Gln Asn Ala Gln Pro Ala
    50                  55                  60

Leu Met Ala Thr Ser Met Ala Ala Leu Ala Ala Leu Glu Val Glu Gly
65                  70                  75                  80

Leu Gly Ile Ala Thr Ala Ser Phe Val Ala Gly His Ser Leu Gly Glu
                85                  90                  95

Tyr Ser Ala Leu Cys Ala Ala Lys Ser Leu Lys Leu Ser Asp Thr Ala
            100                 105                 110

Arg Leu Leu Arg Ile Arg Gly Gln Ala Met Gln Glu Ala Val Pro Val
        115                 120                 125

Gly Val Gly Ala Met Ala Ala Leu Leu Gly Leu Asp Tyr Asp Thr Ala
    130                 135                 140

Val Glu Val Ala His Glu Ala Ala Gln Gly Glu Val Cys Gln Ala Ala
145                 150                 155                 160

Asn Asp Asn Asp Pro Ala Gln Val Val Ser Gly His Lys Ala Ala
                165                 170                 175

Val Glu Arg Ala Val Glu Ile Ala Lys Gly Arg Gly Ala Lys Arg Ala
            180                 185                 190

Ile Leu Leu Pro Val Ser Ala Pro Phe His Cys Ala Leu Met Gln His
        195                 200                 205

Ala Ala Ser Val Met Ser Glu Ala Leu Ala Ala Val Ile Glu Ala
    210                 215                 220

Pro Val Cys Pro Val Val Asn Val Arg Ala Glu Ala Val Ser Glu
225                 230                 235                 240

Pro Asp Arg Ile Arg Ala Leu Leu Val Ala Gln Val Thr Gly Ala Val
                245                 250                 255

Arg Trp Arg Glu Ser Val Met Trp Met Glu Asn Ala Gly Val Asp Glu
            260                 265                 270

Phe Trp Glu Ile Gly Ala Gly Lys Ala Leu Ser Gly Met Ile Lys Arg
        275                 280                 285

Ile Ala Lys Gly Ala Ala Thr Arg Ala Ile Gly Thr Pro Glu Asp Val
    290                 295                 300

Ala Ala Ala Ala Thr Ala
305                 310

<210> SEQ ID NO 24
<211> LENGTH: 323
<212> TYPE: PRT
<213> ORGANISM: Rhodobacter sphaeroides

<400> SEQUENCE: 24

```
Met Thr Ile Arg Ala Val Val Arg Gly Val Gly His Tyr Leu Pro Asp
1               5                   10                  15

Arg Val Val Pro Asn Ser Glu Leu Glu Ala Ile Val Glu Thr Thr Asp
            20                  25                  30

Glu Trp Ile Arg Thr Arg Ser Gly Ile Glu Arg Arg His Phe Ala Ala
        35                  40                  45

Glu Gly Gln Thr Thr Ser Asp Leu Ala Ala Arg Ala Arg Ala Ala
    50                  55                  60

Leu Glu Asp Ala Gly Leu Gln Pro Asp Asp Ile Asp Thr Leu Ile Val
65                  70                  75                  80

Ala Thr Ser Thr Ala Asp Leu Thr Phe Pro Ser Ala Ala Thr Met Val
                85                  90                  95

Gln Ala Ala Leu Gly Met Thr Arg Gly Phe Ala Phe Asp Val Gln Ala
                100                 105                 110

Val Cys Ala Gly Phe Val Tyr Ala Leu Ala Asn Ala Asp Ala Leu Ile
            115                 120                 125

Arg Ser Gly Gln Ala Gln Arg Val Leu Val Ile Gly Ala Glu Thr Phe
130                 135                 140

Ser Arg Leu Met Asp Trp Asn Asp Arg Ala Thr Cys Val Leu Phe Gly
145                 150                 155                 160

Asp Gly Ala Gly Ala Val Val Leu Glu Gly Thr Glu Ser Ala Gly Thr
                165                 170                 175

Ser Ala Asp Arg Gly Ile Leu Ala Thr Asp Leu His Ser Asp Gly Arg
            180                 185                 190

Phe Lys Asp Leu Leu Tyr Val Asp Gly Gly Ser Ser Thr Gly Thr Thr
        195                 200                 205

Gly His Leu Arg Met Gln Gly Arg Glu Val Phe Arg His Ala Val Glu
    210                 215                 220

Lys Leu Ala Glu Thr Ala His Thr Ala Leu Glu Lys Ala Gly Leu Gly
225                 230                 235                 240

Ala Gly Asp Val Asp Trp Ile Val Pro His Gln Ala Asn Leu Arg Ile
                245                 250                 255

Ile Ser Ala Thr Ala Gln Arg Met Gln Val Pro Met Asp Arg Val Ile
            260                 265                 270

Leu Thr Val Gln Asp His Gly Asn Thr Ser Ala Ala Ser Ile Pro Leu
        275                 280                 285

Ala Leu Ser Val Gly Lys Ala Arg Gly Gln Ile Lys Glu Gly Asp Leu
    290                 295                 300

Leu Val Thr Glu Ala Ile Gly Gly Gly Leu Ala Trp Gly Ser Val Val
305                 310                 315                 320

Leu Arg Trp
```

<210> SEQ ID NO 25
<211> LENGTH: 28
<212> TYPE: DNA
<213> ORGANISM: Artificial Sequence
<220> FEATURE:
<223> OTHER INFORMATION: accA forward primer

<400> SEQUENCE: 25
gctctagatt cctccggcgc tcgtgtgg        28

<210> SEQ ID NO 26

<210> SEQ ID NO 26
<211> LENGTH: 30
<212> TYPE: DNA
<213> ORGANISM: Artificial Sequence
<220> FEATURE:
<223> OTHER INFORMATION: accA reverse primer

<400> SEQUENCE: 26
aactgcagtc acgccgcgag gcccttcgac         30

<210> SEQ ID NO 27
<211> LENGTH: 27
<212> TYPE: DNA
<213> ORGANISM: Artificial Sequence
<220> FEATURE:
<223> OTHER INFORMATION: accBC forward primer

<400> SEQUENCE: 27
caagcttgtt gtccggcgtc ttgtagc         27

<210> SEQ ID NO 28
<211> LENGTH: 27
<212> TYPE: DNA
<213> ORGANISM: Artificial Sequence
<220> FEATURE:
<223> OTHER INFORMATION: accBC reverse primer

<400> SEQUENCE: 28
gctctagacg gcgaaatcct catccac         27

<210> SEQ ID NO 29
<211> LENGTH: 20
<212> TYPE: DNA
<213> ORGANISM: Artificial Sequence
<220> FEATURE:
<223> OTHER INFORMATION: accD forward primer

<400> SEQUENCE: 29
gtctcctccg aagcaggcgc         20

<210> SEQ ID NO 30
<211> LENGTH: 22
<212> TYPE: DNA
<213> ORGANISM: Artificial Sequence
<220> FEATURE:
<223> OTHER INFORMATION: accD reverse primer

<400> SEQUENCE: 30
tcactcggcg gccttgtcgt cg         22

<210> SEQ ID NO 31
<211> LENGTH: 32
<212> TYPE: DNA
<213> ORGANISM: Artificial Sequence
<220> FEATURE:
<223> OTHER INFORMATION: fabD forward primer

<400> SEQUENCE: 31
gctctagaag gatcatcata tccgcacagt tc         32

<210> SEQ ID NO 32
<211> LENGTH: 29
<212> TYPE: DNA
<213> ORGANISM: Artificial Sequence
<220> FEATURE:
<223> OTHER INFORMATION: fabD reverse primer

<400> SEQUENCE: 32
aactgcagtc aggccgtggc ggcagccgc                                     29

<210> SEQ ID NO 33
<211> LENGTH: 33
<212> TYPE: DNA
<213> ORGANISM: Artificial Sequence
<220> FEATURE:
<223> OTHER INFORMATION: fabH forward primer

<400> SEQUENCE: 33
ggggtaccct atgcccgcaa cggtctcagc ctc                                33

<210> SEQ ID NO 34
<211> LENGTH: 28
<212> TYPE: DNA
<213> ORGANISM: Artificial Sequence
<220> FEATURE:
<223> OTHER INFORMATION: fabH reverse primer

<400> SEQUENCE: 34
gctctagatg aagcacggat tccaccag                                      28

<210> SEQ ID NO 35
<211> LENGTH: 1686
<212> TYPE: DNA
<213> ORGANISM: Escherichia coli

<400> SEQUENCE: 35
ttgaagaagg tttggcttaa ccgttatccc gcggacgttc cgacggagat caaccctgac    60
cgttatcaat ctctggtaga tatgtttgag cagtcggtcg cgcgctacgc cgatcaacct   120
gcgtttgtga atatggggga ggtaatgacc ttccgcaagc tggaagaacg cagtcgcgcg   180
tttgccgctt atttgcaaca agggttgggg ctgaagaaag gcgatcgcgt tgcgttgatg   240
atgcctaatt tattgcaata tccggtggcg ctgtttggca ttttgcgtgc cgggatgatc   300
gtcgtaaacg ttaacccgtt gtataccccg cgtgagcttg agcatcagct taacgatagc   360
ggcgcatcgg cgattgttat cgtgtctaac tttgctcaca cactggaaaa agtggttgat   420
aaaaccgccg ttcagcacgt aattctgacc cgtatgggcg atcagctatc tacggcaaaa   480
ggcacggtag tcaatttcgt tgttaaatac atcaagcgtt tggtgccgaa ataccatctg   540
ccagatgcca tttcatttcg tagcgcactg cataacggct accggatgca gtacgtcaaa   600
cccgaactgg tgccggaaga tttagctttt ctgcaataca ccggcggcac cactggtgtg   660
gcgaaaggcg cgatgctgac tcaccgcaat atgctggcga acctggaaca ggttaacgcg   720
acctatggtc cgctgttgca tccgggcaaa gagctggtgg tgacggcgct gccgctgtat   780 cacattttg ccctgaccat taactgcctg ctgtttatcg aactgggtgg gcagaacctg   840
cttatcacta acccgcgcga tattccaggg ttggtaaaag agttagcgaa atatccgttt   900
accgctatca cgggcgttaa caccttgttc aatgcgttgc tgaacaataa agagttccag   960
cagctggatt tctccagtct gcatcttttc gcaggcggtg ggatgccagt gcagcaagtg  1020
gtggcagagc gttgggtgaa actgaccgga cagtatctgc tggaaggcta tggccttacc  1080
gagtgtgcgc cgctggtcag cgttaaccca tatgatattg attatcatag tggtagcatc  1140 ggttttgccgg tgccgtcgac ggaagccaaa ctggtggatg atgatgataa tgaagtacca  1200
ccaggtcaac cgggtgagct ttgtgtcaaa ggaccgcagg tgatgctggg ttactggcag  1260
cgtcccgatg ctaccgatga aatcatcaaa aatggctggt acacaccggg cgacatcgcg  1320

```
gtaatggatg aagaaggatt cctgcgcatt gtcgatcgta aaaaagacat gattctggtt    1380
tccggtttta acgtctatcc caacgagatt gaagatgtcg tcatgcagca tcctggcgta    1440
caggaagtcg cggctgttgg cgtaccttcc ggctccagtg gtgaagcggt gaaaatcttc    1500
gtagtgaaaa aagatccatc gcttaccgaa gagtcactgg tgacttttttg ccgccgtcag   1560 ctcacgggat acaaagtacc gaagctggtg gagtttcgtg atgagttacc gaaatctaac    1620
gtcggaaaaa ttttgcgacg agaattacgt gacgaagcgc gcggcaaagt ggacaataaa    1680
gcctga                                                               1686

<210> SEQ ID NO 36
<211> LENGTH: 27
<212> TYPE: DNA
<213> ORGANISM: Artificial Sequence
<220> FEATURE:
<223> OTHER INFORMATION: fadD upstream forward primer

<400> SEQUENCE: 36
gtcgacagtg acgcgcttcg caacctt                                        27

<210> SEQ ID NO 37
<211> LENGTH: 27
<212> TYPE: DNA
<213> ORGANISM: Artificial Sequence
<220> FEATURE:
<223> OTHER INFORMATION: fadD upstream reverse primer

<400> SEQUENCE: 37
gaattcaaca gcgccaccgg atattgc                                        27

<210> SEQ ID NO 38
<211> LENGTH: 27
<212> TYPE: DNA
<213> ORGANISM: Artificial Sequence
<220> FEATURE:
<223> OTHER INFORMATION: fadD downstream forward primer

<400> SEQUENCE: 38
gaattcgtgg tgaagcggtg aaaatct                                        27

<210> SEQ ID NO 39
<211> LENGTH: 27
<212> TYPE: DNA
<213> ORGANISM: Artificial Sequence
<220> FEATURE:
<223> OTHER INFORMATION: fadD downstream reverse primer

<400> SEQUENCE: 39
gcatgcagtt gaatcaaccc cagctgc                                        27
```

STRAIN SECRETING FATTY ACIDS BY PHOSPHOLIPASE AND METHOD FOR PRODUCING FATTY ACIDS USING IT

CROSS-REFERENCE TO RELATED APPLICATION

This application claims the benefit of Korean Patent Application No. 10-2014-0067747, filed on Jun. 3, 2014, in the Korean Intellectual Property Office, the disclosure of which is incorporated herein in its entirety by reference.

BACKGROUND

1. Field

The present disclosure relates to a recombinant bacterial strain extracellularly secreting fatty acids by using phospholipase activity and a method of producing fatty acids by using the same.

2. Description of the Related Art

Modern industries have still heavily depended on fossil fuels for use as source materials for chemical industries and as energy sources. The use of fossil fuels causes economic problems, including an increase in costs due to limited fossil deposits, and various environmental problems, including an increase in the concentration of carbon dioxide in air. The claim that future technology to brace for various environmental problems caused by the use of fossil fuels and depletion of fossil is needed still gains attention with social awareness. However, until now, new renewable energy having sustainability and economic competitiveness, which can replace the existing fossil fuels, has not been developed.

Recently, as a way to develop new renewable energy, the research to produce fatty acids either by fixing carbon dioxide or by reusing waste organic materials is being carried out. Fatty acids are converted into fatty acid ester through available chemical reactions, and fatty acids and derivatives thereof can be used as new renewable energy that replaces the oil from fossil fuel. Accordingly, in view of economic competitiveness due to an improvement of fatty acid producing technology and socio-politics, the practical use of fatty acids and derivatives thereof as an alternative energy source may be realized sooner than expected.

Unsaturated fatty acids are high value-added materials due to their use as a source material for medical products, cosmetic products, animal feeds, and heath supplements, as well as energy sources. In the past, only fatty acids with pre-determined composition could be produced by using, for example, plants and microalgae. However, technical advances in synthetic biotechnology, allow the composition of a fatty acid to be changed according to a desired purpose, and in particular, now, it is possible to increase the amount of useful unsaturated fatty acids to substantial levels.

The first-generation fatty acid production method uses neutral fat-rich plants to obtain fatty acids. However, this method requires a big land that could be used for crop culture otherwise, and accordingly, in consideration of global environmental change and imbalanced food production, the first-generation method is likely to face ethical problems. In this regard, in the future, the development of the fatty acid production by this method needs to be focused on use of places such as desert, mountainous regions, or the sea.

Microalgae are able to store lipid in large quantity per cell. However, up until now, it is difficult to readily apply the genetic methods thereto, and accordingly, additional increase of fatty acid productivity may not be feasible by using metabolic engineering methods. In addition, in the case of typical processes of producing fatty acids from plants and microalgae, processes for the pre-treatments of cells and the extractions of fatty acids are expensive and cause secondary contamination.

Korean Publication Patent No. 10-2009-0068266 provides information about polypeptides having phospholipase activity, nucleic acids coding for the polypeptides, and antibodies binding to the phospholipase. This publication provides an industrial method of degumming oil from a composition containing phospholipase. Korean Publication Patent No. 10-2011-0034116 provides a method of producing phospholipid, of which composition is changed by substituting a fatty acid of phospholipid by using immobilized phospholipase. The present disclosure is similar to these two publications in terms of the use of phospholipase as an active ingredient. However, the present disclosure, unlike these publications, uses phospholipase to secrete more fatty acids from bacterial cell that was genetically modified to synthesize more fatty acids.

The fact that fatty acids are extracellularly secreted by the action of thioesterase has been well known in many publications including Lennen and Pfleger (2012. Cell. 30: 659-667.). Like the present disclosure, US Publication Patent No. 2012/0237987A1 also discloses the secretion of fatty acids out of cyanobacterial cell. However, this publication is different from the present disclosure in that thioesterase, which is an enzyme using an acyl-acyl carrier protein (acyl-ACP) as a substrate, is used to induce the secretion of fatty acids. In addition, the present disclosure is different from the existing invention in that instead of expression of thioesterase in cytoplasm, phospholipase is expressed in a periplasmic space between an inner membrane and an outer membrane to efficiently decompose membrane phospholipids to form free fatty acids, which are then easily secreted out of the bacterial cell.

The above-mentioned background is presented herein only to help understanding of the background of the present disclosure, and shall not be considered to one of ordinary skill in the art as approving that the presented background is the prior art.

SUMMARY

The inventors of the present disclosure have made efforts to develop a novel method to secrete fatty acids, which are synthesized in bacterial cytoplasm, out of the cell with high efficiency. As a result, the inventors have designed a technology of inducing secretion of fatty acids, which are decomposed from membrane phospholipids by the activity of foreign phospholipase expressed in a periplasmic space of bacterial cell. When the activity level of phospholipase is too high, apoptosis may occur. Accordingly, they used a method in which the expression of phospholipase is adjusted and at the same time, synthesis of fatty acids and subsequently phospholipids being a substrate of phospholipase is increased, thereby completing the present disclosure.

Thus, the present disclosure is to provide a strain extracellularly secreting fatty acids by expressing phospholipase in the periplasmic space of a cell.

The present disclosure also provides a method of constructing the strain.

The present disclosure also provides a method of producing fatty acids by using the strain.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
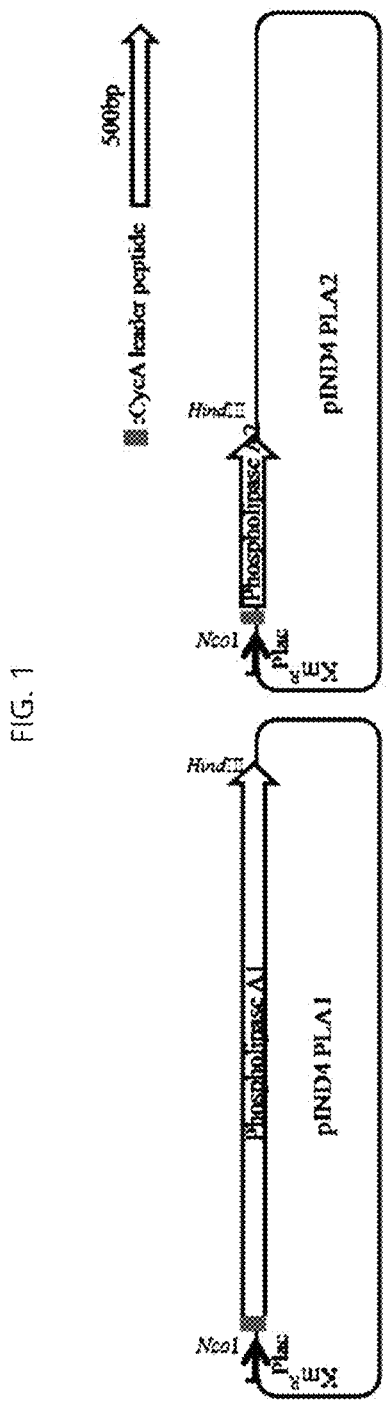
FIG. 1 illustrates a schematic diagram of pIND4-cycA-pLA1 and pIND4-cycApLA2, which are pIND4-derived constructs used to respectively express *Arabidopsis thaliana*-derived phospholipase A1 and phospholipase A2 in the periplasmic space of bacterial cell. To induce the expression of phospholipase in the periplasmic space, a leader peptide sequence having 23 amino acids of CycA N-terminus was ligated to an N-terminus position of each of these two phospholipases.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects.

An aspect of the present disclosure provides a strain extracellularly secreting fatty acids by expressing phospholipase in a periplasmic space of bacterial cell.

Another aspect of the present disclosure provides a method of producing a strain secreting fatty acids, including the preparation of a plasmid construct expressing phospholipase.

Another aspect of the present disclosure provides a method of producing fatty acids, including culturing the strain in medium.

The inventors of the present disclosure have strenuously made efforts to develop a fatty acid-secretion bacterial strain with high efficiency that continuously secretes fatty acids without disruption or apoptosis of bacterial cells. As a result, they found that when phospholipase is expressed in periplasmic space of a bacterial cell, the phospholipase selectively decomposes phospholipid to form free fatty acids, which are subsequently secreted into the culture medium.

Microorganism, including *Escherichia coli*, and plants have a type II fatty-acid synthesis system that mediates a de novo synthesis of fatty acids by inducing individual reactions due to the independent existence of enzymes involved in fatty acid biosynthesis. In comparison, however, animals have a type I fatty acid synthesis system in which the active site of each enzyme in every phases of the fatty acid biosynthesis is found in a separate domain of a single large polypeptide (White et al. 2005. Annu Rev Biochem. 74: 791-831.). Accordingly, bacterial fatty acid biosynthesis can be easily restructured by changing the expression of particular enzyme, and ultimately, the production level of fatty acids and the composition thereof may be easily altered.

The composition of fatty acids acts as a major factor, determining membrane fluidity and membrane permeability, which are main physical properties of cell membrane. When the physical properties of cell membrane are changed, the function of a membrane protein may be affected, leading to change in, for example, electron transfer, cell signal transduction, selective permeability of a material, which are major functions of cell membrane. Regarding the composition of fatty acids, a degree of unsaturation of fatty acids most heavily affects the membrane property. The unsaturation of fatty acids may occur in vivo in two different manners: in one manner, unsaturated fatty acids are synthesized by the sequential reactions of β-hydroxydecanoyl-ACP dehydratase/isomerase (FabA) and 8-ketoacyl ACP synthase I (FabB) during elongation of initial fatty acid synthesis (Feng and Cronan. 2009. J Biol Chem. 284: 29526-29535); in the other manner, unsaturated fatty acids are synthesized by an action of fatty acid desaturase (desA/desB/desC/desD) using saturated fatty acid that is already synthesized (Wada and Murata. 1990. Plant Physiol. 92: 1062-1069.). Even when fatty acids are produced for industrial purpose, the composition of fatty acids is also an important issue. The metabolic flow for fatty acid biosynthesis and the composition of fatty acids may be controlled by redesigning the expression of the associated enzymes. That is, when the expression of β-ketoacyl ACP synthase I (FabB) is increased or foreign fatty acid desaturase is expressed, the degree of fatty acid unsaturation of cell membrane may be increased and at the same time, the amount of a particular unsaturated fatty acid having high industrial values may be increased.

When the concentration of produced fatty acids is increased in cell, feedback inhibition for the synthesis of new fatty acids may occur (Zhang and Rock. 2009. 50(Suppl): S115-S119). That is, fatty acids accumulated inside cell are bound to a transcriptional regulatory factor FadR not only to repress the expression of the genes coding for the fatty acid biosynthesis enzymes but also to activate the expression of the genes coding for the fatty acid degradation enzymes. Accordingly, as a way to suppress the feedback activities by the endogenous fatty acids, extracellular secretion of the free fatty acid may be taken into consideration.

Thioesterase (TesA) cleaves an ester bond between a fatty acid and ACP. When a foreign TesA is expressed in cells, it detaches the fatty acids from ACP so as to induce secretion thereof to the outside of cell (Lennen and Pfleger. 2012. Cell 30: 659-667.). In this case, the efficiency of fatty acid synthesis is increased, and free fatty acids are secreted into medium. Accordingly, centrifugation of culture broth to collect cells for the recovery of cellular fatty acids through the breakage of cells is not needed. However, when thioesterase is used for the extracellular secretion of fatty acids, acyl-ACP is used as a substrate. Thus, it ends up with the secretion of all the cellular fatty acids including their biosynthetic intermediates. In addition, since thioesterase acts inside cytoplasm where acyl-ACP is found, the free fatty acids need to pass through a cellular inner membrane and an outer membrane to come out of the cell, resulting in low efficiency of fatty acid production.

As described above, in the case of TesA, free fatty acids may be accumulated in cell due to the low efficiency of fatty acid production. This may lead to the degradation of free endogenous fatty acids. Moreover, the fatty acids at varying length are obtained because of the low substrate specificity of TesA. However, according to the present disclosure, phospholipase is expressed in the periplasmic space of a bacterial cell so that fatty acids at certain carbon length are quickly, efficiently secreted extracellularly.

The phospholipase may be derived from animals or plants, but is not limited thereto. For example, the phospholipase may be phospholipase A1 or phospholipase A2. For example, the phospholipase may be *Arabidopsis thaliana*-derived phospholipase A1 or phospholipase A2.

The phospholipase gene may be constructed as an expression construct to induce expression thereof in the periplasmic space of a bacterial cell.

How the phospholipase is expressed in the periplasmic space of a cell is not limited. For example, the gene segment coding for the leader peptide of a periplasmic protein (for example, the gene of CycA) is fused to the phospholipase gene, and cloned into an expression construct plasmid. The expression construct is mobilized into a cell through conjugation to express the phospholipase in the periplasmic space of the cell.

Further, to increase the level of fatty acid biosynthesis, the expression plasmid construct may be manufactured in such a manner that acetyl-CoA carboxylase that synthesizes malonyl-CoA from acetyl-CoA, malonyl-CoA:ACP transacylase (FabD) that converts malonyl-CoA into malnoyl-ACP, and β-ketoacyl ACP synthase Ill (FabH) that synthesize C4-ACP through the condensation of acetyl group and malonyl group with the liberation of $CO_2$ are additionally expressed. Because these enzymes are responsible for the synthesis of C4-ACP, which are the elongation intermediates of fatty acid synthesis, the additional expression of these enzymes in cell should increase the metabolic flux of cellular fatty acid synthesis. The fatty acid synthesis may be further increased by blocking a pathway that is not necessary for cell growth, for example, a metabolic pathway for the synthesis of poly-β-hydroxybutyrate (PHB), which is a carbon storage material. By doing so, efficiency of fatty acid production may be maximized.

Fatty acids obtainable from the bacterial strain secreting fatty acids according to the present disclosure are not limited. For example, fatty acids having the carbon number of 16 or more may be obtained. For example, palmitic acids, stearic acids, vaccenic acids, or the like may be obtained with high efficiency.

According to the present disclosure, re-uptake of fatty acids by a bacterial cell may be suppressed. For example, fatty acids secreted into medium in which cells are cultured may be allowed to enter cells through FadL that is a long chain fatty acid transporter and is in charge of re-uptake of fatty acids. In addition, fatty acids may be re-used through the action of long chain fatty acyl-CoA synthetase (FadD).

The suppression of fatty-acid re-uptake may be achieved by deleting a whole sequence or a part thereof of a protein in charge of uptake of fatty acids and/or a protein in charge of re-use of fatty acids.

The strain according to the present disclosure is not limited, and may be, for example, *Escherichia coli*. In some embodiments of the present disclosure, DH5α(pRK-fabD+pIND4-cycApLA1) deposited as Accession No. KCTC12599BP and DH5α(pRK-fabH+pIND4-cycApLA2) deposited as Accession No. KCTC12600BP were used. DH5α(pRK-fabD+pIND4-cycApLA1) and DH5α(pRK-fabH+pIND4-cycApLA2) have been deposited with Korean Research Institute of Bioscience and Biotechnology having the address of 125 Gwahak-ro, Yuseong-gu, Daejeon 305-806, Republic of Korea, under the Access numbers of KCTC12599BP and KCTC12600BP, respectively, on May 23, 2014. The deposits have been made under the terms of the Budapest Treaty and all restrictions imposed by the depositor on the availability to the public of the biological material will be irrevocably removed upon the granting of a patent. However, other bacterial strains having the above-mentioned characteristics for fatty-acid secretion may be generated by using the methods shown in the present disclosure.

In some embodiments, a carbon source may be further added to the medium to increase the amount of fatty acids produced from the bacterial cell that is generated according to the present disclosure. Various carbon sources known in the art may be used as the carbon source. For example, glucose or glycerol may be used as the carbon source. A concentration of the carbon source additionally provided to the medium may be in a range of 0.1% (w/v) to 4.0% (w/v), or 0.4% (w/v) to 2.0% (w/v). When the concentration thereof is outside the lower limits, the increase in production of fatty acids hardly occurs, and when the concentration thereof is outside the upper limits, saturation may occur.

Characteristics and advantages of the present disclosure may be summarized as below:

(i) The present disclosure provides a bacterial strain secreting fatty acids, the bacterial strain inducing extracellular secretion of fatty acids by using phospholipase.

(ii) The present disclosure also provides a method of generating the bacterial strain secreting fatty acids.

(iii) The present disclosure also provides a method of producing fatty acids by using the bacterial strain secreting fatty acids.

(iv) When the production method of fatty acids according to the present disclosure is used, fatty acids extracellularly secreted may be continuously obtained without harvest of cells. Since the secreted fatty acids are continuously obtained, efficiency and stability of this method may be high. Also, fatty acids having specific compositions may be selectively produced by using the phospholipase that has specific substrate specificity. In addition, fatty acids easily secreted according to the present disclosure, unlike in a typical method of obtaining fat from cells or tissues, can be obtained, without the extraction process using an organic solvent in great quantities, by the attachment of free fatty acids to the hydrophobic material. Accordingly, the production method of free fatty acids according to the present disclosure may lead to an economic and environmentally friendly bio-oil production process by using the genetically-engineered bacteria.

EXAMPLES

Example 1: Expression of Phospholipase in Periplasmic Space

Phospholipase is a phospholipid lyase that cleaves a fatty acid from phospholipid, and is classified as type A1, type A2, type C, and type D according to the specificity of the cleavage site. Phospholipase A1 is an enzyme that cleaves a covalent bond at sn-1 position of phospholipid to form a free fatty acid that had once bound to sn-1 position and a phospholipid with only one fatty acid bound thereto, and phospholipase A2 is an enzyme that cleaves a covalent bond at sn-2 position to form a free fatty acid that had once bound to sn-2 position and a phospholipid with only one fatty acid bound thereto. Complementary DNA (cDNA) of phospholipase A1 set forth in SEQ ID NO: 1 and cDNA of phospholipase A2 set forth in SEQ ID NO: 2 were obtained from *Arabidopsis thaliana*. To this end, RNA was extracted from *Arabidopsis thaliana*, and a reverse transcriptase, which is a RNA-dependent DNA polymerase, was used, thereby synthesizing cDNA. A polymerase chain reaction (PCR) was performed using a forward primer set forth in SEQ ID NO: 3 and a reverse primer set forth in SEQ ID NO: 4 while the cDNA is used as a template, thereby obtaining phospholipase A1 gene. The forward primer had a recognition site of restriction enzyme XbaI inserted thereinto, and the reverse primer had a recognition site of restriction enzyme HindIII inserted thereinto. Likewise, while cDNA of *Arabidopsis thaliana* was used as a template, PCR was performed using a forward primer set forth in SEQ ID NO: 5 and a reverse primer set forth in SEQ ID NO: 6, thereby obtaining phospholipase A2 gene. The forward primer also had a recognition site of restriction enzyme XbaI inserted thereinto, and the reverse primer also had a recognition site of restriction enzyme HindIII inserted thereinto.

To express phospholipase A1 and phospholipase A2 in the periplasmic space, the DNA coding for the N-terminus 23 amino acids of CycA, which is cytochrome c2, of SEQ ID NO: 7 were ligated in frame to each of the obtained phospholipase A1 gene and phospholipase A2 gene. To this end, 69 nucleotides corresponding to the N-terminus 23 amino acids of CycA set forth in SEQ ID NO: 8 were used. The leader peptide of CycA is required for the transport of the protein to the periplasmic space. The leader sequence is ligated in frame to the N-terminus of phospholipase and translated, and ultimately, phospholipase can be induced to express in the periplasmic space. PCR was performed using a forward primer of SEQ ID NO: 9 and a reverse primer of SEQ ID NO: 10 while *Rhodobacter sphaeroides* chromosomal DNA was used as a template. The forward primer had a recognition site of restriction enzyme NcoI inserted thereinto, and the reverse primer had a recognition site of restriction enzyme XbaI inserted thereinto. In the process of obtaining cDNA of each of phospholipase A1 and phospholipase A2, the upstream end of DNA contains a XbaI site. This site was employed to ligate the 69-bp CycA gene in frame to the genes of phospholipase. Ligated DNA segment was cleaved by using NcoI and HindIII, and then, cloned onto pIND4 (Alice et al. 2009. Appl Environ Microbiol. 75: 66136615), of which transcription is adjustable through the addition of IPTG, thereby completing preparation of recombinant plasmid.

FIG. 1 illustrates a schematic diagram of pIND4-cycA-pLA1 and pIND4-cycApLA2, which are pIND4-derived plasmid constructs to respectively express *Arabidopsis thaliana*-derived phospholipase A1 and phospholipase A2 in periplasmic space. These two constructs were used to express *Arabidopsis thaliana*-derived phospholipase A1 and phospholipase A2 enzymes of SEQ ID Nos. 11 and 12, respectively: each in *Escherichia coli*. Additionally, a gene coding *Escherichia coli*-derived alkaline phosphatase was ligated in-frame to the C-terminus of each of phospholipase A1 gene and phospholipase A2 gene to allow these enzymes to be ligated with each other during translation. Activity of the alkaline phosphatase from the resulting construct was measured, and as a result, it was confirmed that as expected, expression of both phospholipases was not observed in cytoplasm but observed in periplasmic space.

Example 2: Enhanced Metabolism at the Early Steps of Fatty Acid Biosynthesis

Figure 2:
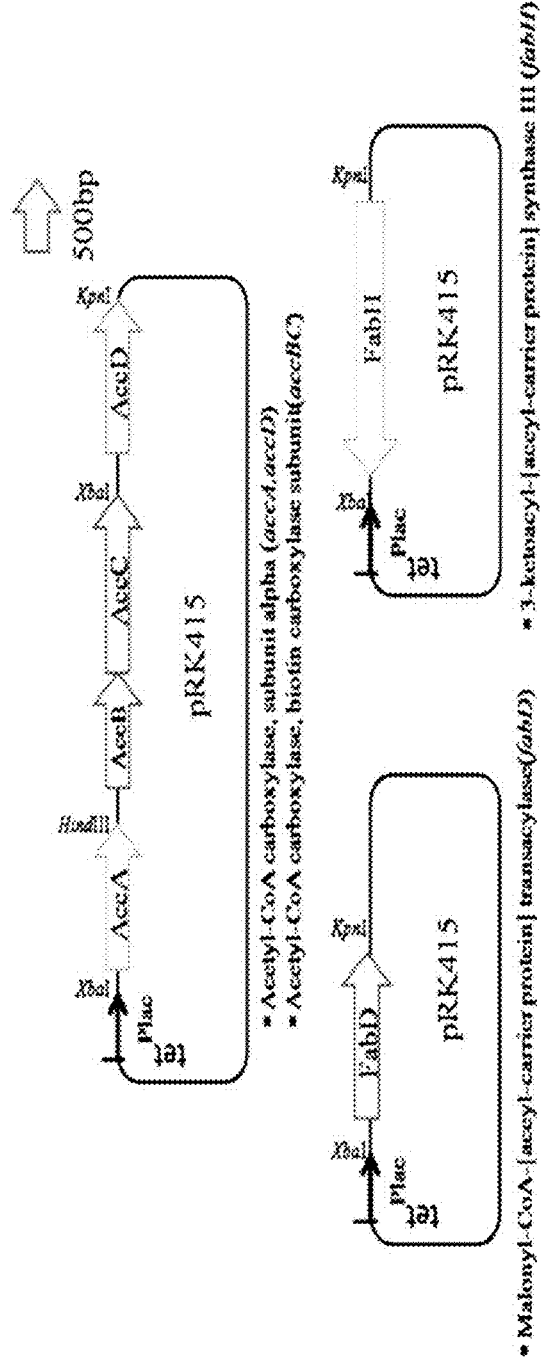
FIG. 2 illustrates a schematic diagram of pRK-accABCD, pRK-fadD and pRK-fadH, which are pRK415-derived plasmid constructs used to respectively express *Rhodobacter sphaeroides*-derived AccABCD, FabD and FabH in *Escherichia coli*.

The genes of acetyl coenzyme-A carboxylase (acetyl-CoA carboxylase, AccABCD) of SEQ ID Nos. from 13 to 16, which is an enzyme complex to synthesize malonyl coenzyme-A (malonyl-CoA) from acetyl coenzyme-A (acetyl-CoA), the gene of malonyl-CoA:ACP transacylase (FabD) of SEQ ID NO: 17, which is an enzyme to convert malonyl-CoA to malnoyl-ACP, and the gene of β-ketoacyl ACP synthase III (FabH) of SEQ ID NO: 18, which is an enzyme to synthesize a precursor C4-ACP for further elongation of fatty acids were obtained from *Rhodobacter sphaeroides*, and these genes were cloned to express the corresponding enzymes each in *Escherichia coli*. Prepared were constructs to express AccABCD of SEQ ID NOs: 19 to 22 consisted of four subunits, FabD of SEQ ID NO: 23, and FabH of SEQ ID NO: 24 in *Escherichia coli*. In this process, PCR was performed using chromosome DNA of *Rhodobacter sphaeroides* as a template, and all base sequences of obtained DNA were examined to verify abnormality thereof. To obtain the gene of AccA, a forward primer of SEQ ID NO: 25 and a reverse primer of SEQ ID NO: 26 were used, and a recognition site of restriction enzyme XbaI was inserted into the forward primer, and a recognition site of restriction enzyme PstI was inserted into the reverse primer. Likewise, to obtain the gene of AccBC, a forward primer of SEQ ID NO: 27 and a reverse primer of SEQ ID NO: 28 were used, and a recognition site of restriction enzyme HindIII was inserted into the forward primer, and a recognition site of restriction enzyme XbaI was inserted into the reverse primer. To obtain the gene of AccD, a forward primer of SEQ ID NO: 29 and a reverse primer of SEQ ID NO: 30 were used, and a recognition site of restriction enzyme XbaI was inserted into the forward primer, and a recognition site of restriction enzyme PstI was inserted into the reverse primer. A DNA segment including the gene of AccA and a DNA segment including the gene of AccD were respectively cloned in XbaI and PstI sites of pBlueScript SK-(Stratagene) to have the recognition site of KpnI at the downstream position. Finally, these three DNA segments were cleaved by using the appropriate restriction enzymes, and then cloned such that they are sequentially ligated on pRK415 (Keen et al. 1988. Gene 70: 191-197), thereby completing the construction of recombinant vector pRK-accABCD expressing AccABCD. To obtain the gene of FabD, a forward primer of SEQ ID NO: 31 and a reverse primer of SEQ ID NO: 32 were used, and the recognition site of restriction enzyme XbaI was inserted into the forward primer and the recognition site of restriction enzyme PstI was inserted into reverse primer. Thereafter, a DNA segment including the gene of FabD was cloned in XbaI and PstI sites of pBlueScript SK- to have the recognition site of KpnI at the downstream position. The DNA segment was cleaved by using the appropriate restriction enzymes, and then cloned on pRK415 vector, completing the construction of a recombinant plasmid pRK-FabD expressing FabD. To obtain the gene of FabH, a forward primer of SEQ ID NO: 33 and a reverse primer of SEQ ID NO: 34 were used, and a recognition site of restriction enzyme KpnI was inserted into the forward primer, and a recognition site of restriction enzyme XbaI was inserted into the reverse primer. The DNA segment was cleaved by using the appropriate restriction enzymes, and then cloned on pRK415 vector, completing the construction of a recombinant plasmid pRK-FabH expressing FabH. By using the above-mentioned method, DNA segments obtained by PCR were all cloned onto pRK415. Ultimately, plasmid constructs that express each of AccABCD, FabD and FabH in *Escherichia coli* were prepared, and FIG. 2 illustrates schematic structures of these constructs.

Example 3: Suppression of Re-Uptake of Secreted Fatty Acids

Figure 3:
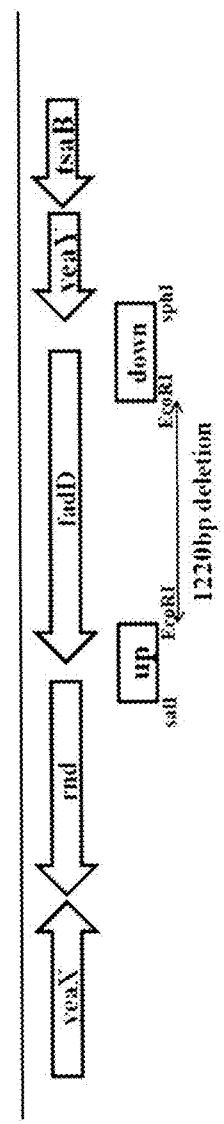
FIG. 3 illustrates a genomic DNA region surrounding the gene of *Escherichia coli* FadD engaging in re-uptake of secreted fatty acids and a method of producing a DNA construct to destroy the gene coding for *Escherichia coli* FadD. Expected functions of surrounding genes are as follows: yeaX, predicted oxidoreductase; rnd, ribonuclease D; yeaY, lipoprotein; tsaB, tRNA threonylcarbamoyladenosine modification protein.

Free fatty acids that are secreted into medium may re-enter a cell through the action of FadL, which is a long chain fatty acid transporter in charge of re-absorption thereof, and may also be re-used through the action of the long chain fatty acyl-CoA synthetase (FadD). Accordingly, to prevent the secreted fatty acids from re-uptake and re-use, the gene of *Escherichia coli* FadD of SEQ ID NO: 35 is destroyed to suppress metabolic procedure degrading the synthesized fatty acids, ultimately improving the efficiency of fatty acid production. To prepare a plasmid construct to destroy the gene of FadD, PCR was performed using chromosome DNA of *Escherichia coli* as a template, and the DNA sequence of the resulting DNA was examined to verity abnormality thereof. To obtain an upstream DNA region of the gene of FadD, a forward primer of SEQ ID NO: 36 and a reverse primer of SEQ ID NO: 37 were used and the forward primer had a recognition site of restriction enzyme SalI inserted thereinto, and the reverse primer had a recognition site of restriction enzyme EcoRI inserted thereinto. Likewise, to obtain a downstream DNA region of the gene of FadD, a forward primer of SEQ ID NO: 38 and a reverse primer of SEQ ID NO: 39 were used, and the forward primer had a recognition site of restriction enzyme EcoRI inserted thereinto, and the reverse primer had a recognition site of restriction enzyme SphI inserted thereinto. DNA segments obtained by each PCR were cloned into pDM4 (Milton et al. 1996. J Bacteriol. 178: 1310-1319), which is a suicide vector. Ultimately, a plasmid construct that has the deletion of 1,220 bp from the gene of FadD was obtained, and a schematic structure thereof is illustrated in FIG. 3. The resulting plasmid construct was mobilized by conjugation to MG1655, which is a subspecies of *Escherichia coli* K-12, and then, homologous recombination on chromosome was induced, and screening was performed thereon by using chloramphenicol that is an antibiotic. Thereafter, a strain with the gene of FadD destroyed by occurrence of double crossover was screened out in the presence of 10% (w/v) concentration of sucrose. The chromosomal structure of the resulting FadD mutant strain was confirmed by PCR using primers of SEQ ID Nos. 34 and 37. In the present example, the gene of FadD was destroyed by suppressing the re-absorption of fatty acids in *Escherichia coli*. However, one of ordinary skill in the art may easily select and control, for example, acyl-ACP synthetase (AasS), instead of FadD, acting in the process of uptake and re-use of fatty acids according to the bacterial species used.

Example 4: Secretion of Fatty Acid by Using Phospholipase and Quantification of Fatty Acids A pRK415-derived recombinant vector expressing the three initial enzymes AccABCD, FabD and FabH for fatty acid synthesis prepared in Example 2 and pIND4-derived recombinant plasmids expressing one of two phospholipases were each transformed into *Escherichia coli*. The pRK415-derived recombinant plasmid was selected and maintained by using tetracycline which is an antibiotic, and the pIND4-derived recombinant plasmid was selected and maintained by using kanamycin which is an antibiotic. These recombinant plasmids were mobilized in *Escherichia coli* by transformation, and then, the resulting six transformed bacterial strains were cultured and maintained by using LB (Luria-Bertani) medium, in which culture method is well known in the art.

To confirm whether fatty acids were extracellularly secreted by the action of phospholipase, fatty acids in the medium were extracted for analysis. Each of the transformed *Escherichia coli* strains was inoculated into 30 ml of LB medium in a 300 ml flask, and then, grown under aerobic condition at a temperature of 37° C. by shaking at a speed of 250 rpm (revolution per minute). According to experimental purposes, glucose or glycerol was added to the LB medium until a concentration thereof reached about 0.4%. When the optical density (at 600 nm) of bacterial culture was about 0.4 to about 1.0, IPTG (Isopropyl β-D-thiogalactopyranoside) was added thereto at a concentration of 0.4 mM to induce the expression of phospholipase, and the bacterial strain was cultured under the same growth conditions until its optical density reached approximately 2.0~4.0. As illustrated in the lower graphs of FIGS. 4 and 5, growth rates of the recombinant bacterial cells were not distinguishable, and bacterial growth was not affected by IPTG treatment. The cultured cell was removed by centrifuging at a gravity of about 7,000 g at a temperature of 4° C. for 10 minutes, and the culture supernatant was filtered by using a filter having an aperture of 0.22 μm to completely remove *Escherichia coli*.

Unlike a typical fatty-acid production method in which cells were directly extracted to obtain fatty acids, this method of obtaining fatty acids secreted into culture medium is not limited. In the present example, fatty acids in medium were extracted by using a mixed organic solvent including chloroform and methanol at a ratio of 2:1. However, to minimize the use of the organic solvent, a solid phase extraction may be used in which fatty acids are obtained by passage through a column consisting of a hydrophobic material, such as C18.

To measure the composition and amount of free fatty acids, the fatty acids were converted into fatty acid methyl ester (FAME) by methyl-esterification using methanolic HCl according to the well-known method (Benning and Somerville. 1992. J Bacteriol. 174: 2352-2360), and FAME was measured by gas chromatography (GC). In this regard, as internal standard (IS), pentadecanoic acid (C15), which had not been found in *Escherichia coli*, was added thereto. The obtained FAME was quantified by using the calibration curve of a corresponding standard material.

Figure 4:
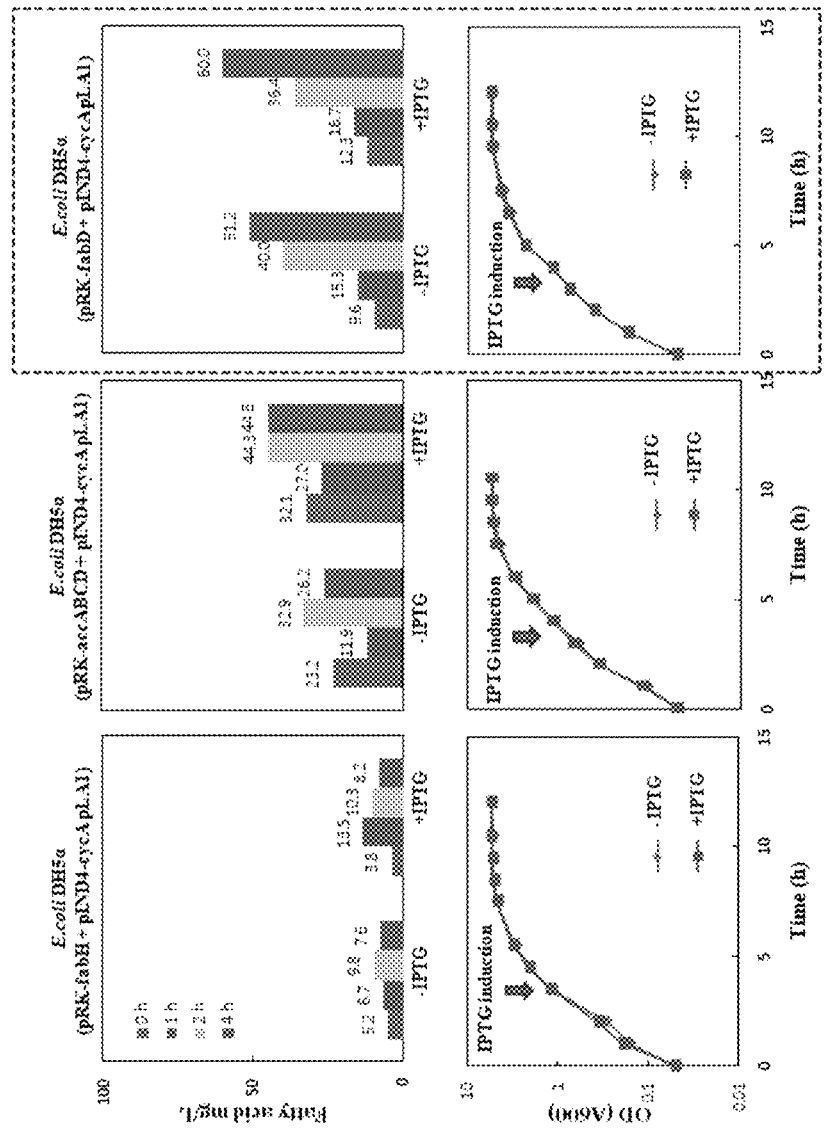
FIG. 4 shows a graph of the concentration of secreted fatty acids when each of AccABCD, FabD and FabH was simultaneously expressed in a strain expressing phospholipase A1. The three recombinant strains were grown in LB medium with or without addition of IPTG. The upper graphs show quantitative analysis results of fatty acids secreted into medium in a unit of mg/L determined by gas chromatography (GC), and the lower graphs are of corresponding growth profiles.
Figure 5:
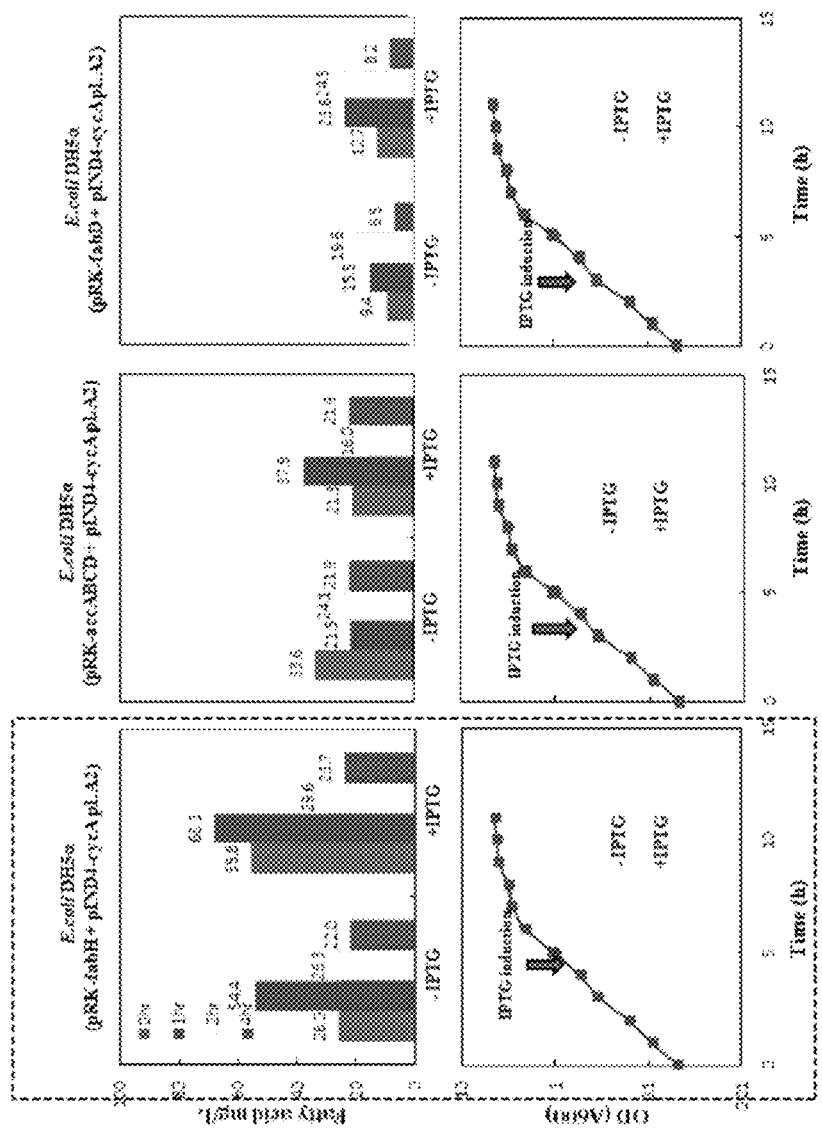
FIG. 5 shows a graph of the concentration of secreted fatty acids when each of AccABCD, FabD and FabH was simultaneously expressed in a strain expressing phospholipase A2. The three recombinant strains were grown in LB medium with or without addition of IPTG. The upper graphs show quantitative analysis results of fatty acids secreted into the medium in a unit of mg/L determined by GC, and the lower graphs are of corresponding growth profiles.

GC results of free fatty acids extracellularly secreted are shown in upper graphs of FIGS. 4 and 5. The major composition of secreted fatty acids included palmitic acid (C16) and stearic acid (C18), which are saturated fatty acids, and cis-vaccenic acid (C18:1Δ11), which is a unsaturated fatty acid, and the amount of whole fatty acids which were assumed to have been present in medium was calculated by using the ratio of the recovered level of IS to the initial level of IS. It is well known that when this experiment performs with the wild-type strain of *Escherichia coli* under the conditions similar to those described above, fatty acids are hardly secreted. However, in the case of the recombinant bacterial cells, it was confirmed that free fatty acids were secreted into culture medium. The strain expressing phospholipase A1 showed an increase of fatty acid production efficiency by about 10% to 20% after the addition of IPTG, and the strain expressing phospholipase A2 showed an increase of fatty acid production efficiency by about 30% to 50% after the addition of IPTG. Even when IPTG was not used, fatty acids were secreted due to the activity of phospholipase expressed at basal level. Accordingly, it is assumed that when the strain expressing phospholipase A1 is used, even when IPTG, which causes an increase in manufacturing costs, is not used, free fatty acids can be produced at significant level compared with that observed after IPTG treatment.

In the case of the strain expressing phospholipase A1, when FabD was expressed together, the amount of fatty acids produced was greater than those in the other two cases, and 4 hours after the addition of IPTG, the amount of fatty acids was greatest, about 60 mg/L. In the case of the strain expressing phospholipase A2, when FabH was expressed together, the amount of fatty acids produced was greater than those in the other two cases, and one hour after the addition of IPTG, the amount of fatty acids was greatest, about 68 mg/L.

Example 5: Effects of Carbon Source Used

A carbon source was additionally provided to LB medium to increase the fatty acid production efficiency. In this experiment, glucose and glycerol were used as additional carbon sources, and strains used herein were the strain simultaneously expressing phospholipase A1 and FabD showing the highest fatty-acid production efficiency in Example 4 and the strain simultaneously expressing phospholipase A2 and FabH showing the highest fatty-acid production efficiency in Example 4.

Figure 6:
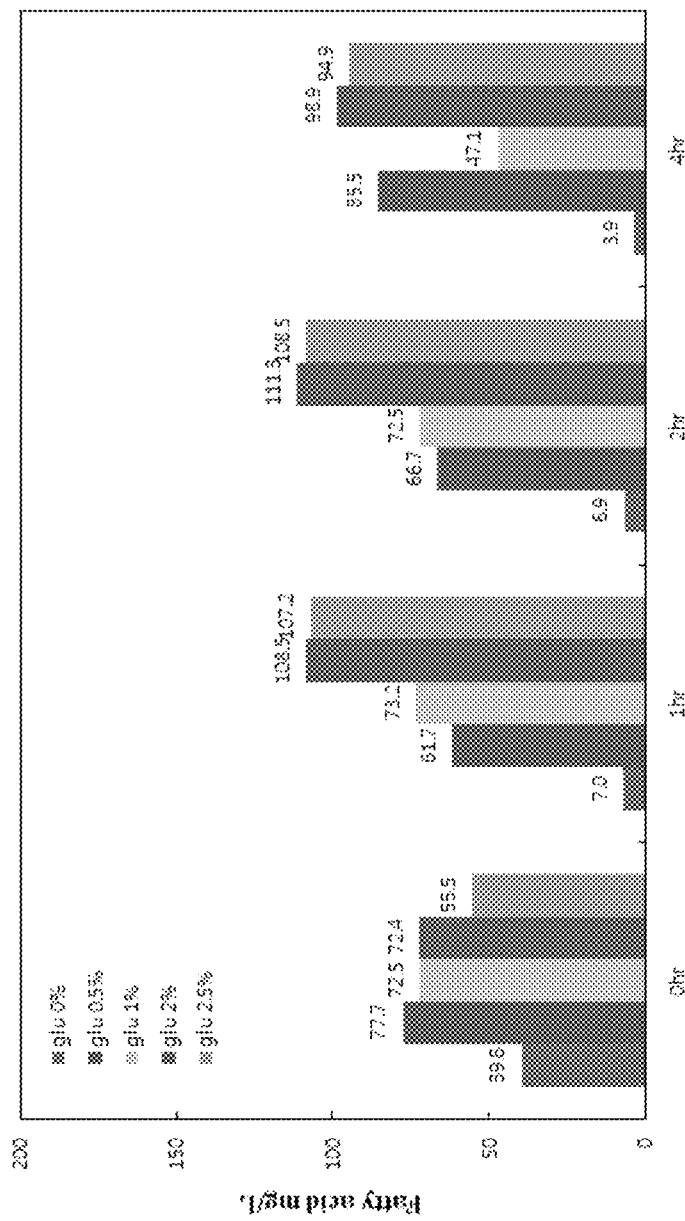
FIG. 6 shows a graph of the concentration of fatty acids according to time, the fatty acid secreted by a recombinant strain simultaneously expressing phospholipase A1 and FabD in LB medium supplemented with varying concentrations of glucose. The fatty acids secreted into culture medium were quantitatively assayed by GC and the results were expressed in the unit of mg/L.

FIG. 6 shows experimental results obtained by growing the strain simultaneously expressing phospholipase A1 and FabD, at varying concentrations of glucose added. The results show that the fatty acid production efficiency began to increases at a concentration of glucose, 0.5% (w/v), and then, increased in proportion to the glucose concentration. However, at the glucose concentration of 2.0% (w/v) or more, the increase in fatty acid production did not occur. With the same strain simultaneously expressing phospholipase A1 and FabD, the amount of fatty acids produced was greatest, about 111 mg/L, at a glucose concentration of 2.0% (w/v), and about 2 hours after the addition of IPTG.

Figure 7:
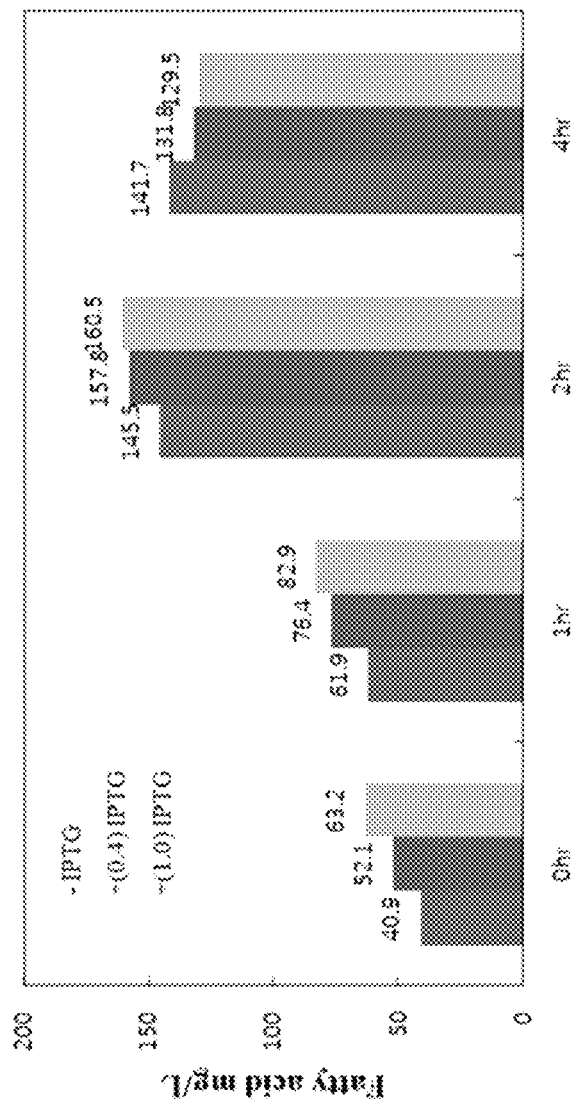
FIG. 7 shows a graph of the concentration of fatty acids according to time, the fatty acids secreted by a recombinant strain simultaneously expressing phospholipase A1 and FabD grown in LB medium supplemented with glycerol having a concentration of 0.4% (w/v). The fatty acids secreted into culture medium were quantitatively assayed by GC and the results were expressed in the unit of mg/L.

Glycerol is produced as a by-product when fatty acids are produced from plant oil, and is very inexpensive compared with glucose. FIG. 7 shows the results of an experiment performed to confirm the effects of glycerol on fatty acid production of the strain simultaneously expressing phospholipase A1 and FabD. In this experiment, the glycerol concentration was fixed at 0.4% (w/v) and IPTG was added at different times: IPTG was not added; IPTG was added when the culture optical density at 600 nm was about 0.4; and IPTG was added when the culture optical density at 600 nm was about 1.0. Experimental results show that in these three cases, the production efficiency of fatty acids was not distinguishable. These results are the same as obtained in Example 4 in which the strain expressing phospholipase A1 showed an increase of fatty acid production efficiency by about 10% to 20% after the addition of IPTG. However, the production efficiency of fatty acids was largely dependent on a carbon source. For example, in case of the strain simultaneously expressing phospholipase A1 and FabD, the amount of produced fatty acids in LB medium was about 60 mg/L, and when 2.0% (w/v) concentration of glucose was added thereto, the amount of produced fatty acids was about 111 mg/L, and when 0.4% (w/v) concentration of glycerol was added thereto, the amount of produced fatty acids was about 161 mg/L. Accordingly, it was confirmed that from among carbon sources used in this experiment, glycerol increased the fatty acid production efficiency most effectively.

Figure 8:
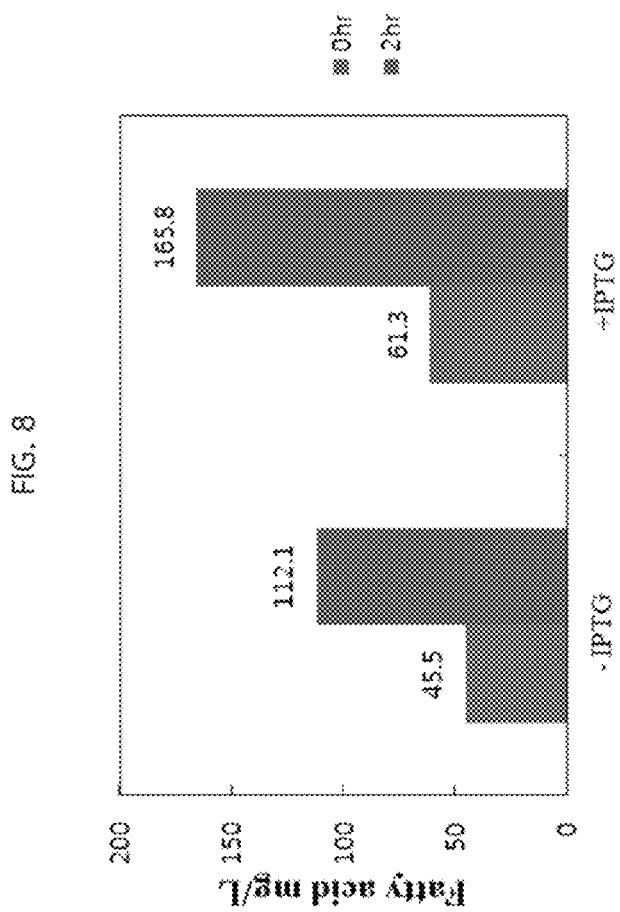
FIG. 8 shows a graph of the concentration of fatty acids secreted by a recombinant strain simultaneously expressing phospholipase A2 and FabH, the recombinant strain grown in LB medium supplemented with glycerol having a concentration of 0.4% (w/v). The fatty acids secreted into the LB medium were quantitatively assayed by GC and the results were expressed in the unit of mg/L.

Under a condition in which glycerol was added in a concentration of 0.4% (w/v), which was confirmed as the most effective condition in this experiment, the strain simultaneously expressing phospholipase A2 and FabH was examined. As shown in FIG. 8, the strain expressing phospholipase A2 showed about 50% increase in fatty acid production efficiency, and 2 hours after the addition of IPTG, the amount of the produced fatty acids was greatest, about 166 mg/L. Accordingly, it was confirmed that in the same conditions, the strain simultaneously expressing phospholipase A2 and FabH also showed productivity similar to that of the strain simultaneously expressing phospholipase A1 and FabD.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments. While one or more exemplary embodiments have been described with reference to the figures, it will be understood by those of ordinary skill in the art that various changes in form and details may be made therein without departing from the spirit and scope as defined by the following claims.

ACCESSION NUMBERS

Name of Depository Institution: Korea Research Institute of Bioscience & Biotechnology
Accession Number: KCTC12599BP
Accession Date: May 26, 2014
Name of Depository Institution: Korea Research Institute of Bioscience & Biotechnology
Accession Number: KCTC12600BP
Accession Date: May 26, 2014

What is claimed is:

1. A bacterial strain, which comprises a gene coding cytochrome c2 signal peptide ligated to a gene coding phospholipase, for secreting fatty acids toward the outside a cell by expressing the phospholipase in the periplasmic space of a bacterial cell, wherein the bacterial strain is DH5α(pRK-fabD+pIND4-cycApLA1) deposited under the Access number of KCTC12599BP or DH5α(pRK-fabH+pIND4-cycApLA2) deposited under the Access number of KCTC12600BP.

2. A method of producing fatty acids, the method comprising culturing the strain of claim 1 in medium.

3. The method of claim 2, wherein the medium comprises a carbon source, wherein the carbon source is selected from the group consisting of glucose and glycerol.

4. The method of claim 2, wherein the carbon source in medium has an amount of 0.1% (w/v) to 4.0% (w/v).

* * * * *